(12) United States Patent
Sra et al.

(10) Patent No.: US 10,881,316 B2
(45) Date of Patent: Jan. 5, 2021

(54) AUTOMATICALLY DETERMINING 3D CATHETER LOCATION AND ORIENTATION USING 2D FLUOROSCOPY ONLY

(71) Applicants: Jasbir Sra, Pewaukee, WI (US); Barry Belanger, Chenequa, WI (US); Mark Palma, Fitchburg, WI (US); Donald Brodnick, Cedarburg, WI (US); Bruce Langenbach, Milwaukee, WI (US)

(72) Inventors: Jasbir Sra, Pewaukee, WI (US); Barry Belanger, Chenequa, WI (US); Mark Palma, Fitchburg, WI (US); Donald Brodnick, Cedarburg, WI (US); Bruce Langenbach, Milwaukee, WI (US)

(73) Assignee: APN Health, LLC, Pewaukee, WI (US)

( * ) Notice: Subject to any disclaimer, the term of this patent is extended or adjusted under 35 U.S.C. 154(b) by 0 days.

(21) Appl. No.: 15/924,761

(22) Filed: Mar. 19, 2018

(65) Prior Publication Data

US 2018/0296117 A1 Oct. 18, 2018

Related U.S. Application Data

(63) Continuation of application No. 13/607,163, filed on Sep. 7, 2012, now Pat. No. 9,986,931.
(Continued)

(51) Int. Cl.
*A61B 5/0456* (2006.01)
*A61B 6/00* (2006.01)
(Continued)

(52) U.S. Cl.
CPC ............ *A61B 5/0456* (2013.01); *A61B 5/061* (2013.01); *A61B 5/7289* (2013.01); *A61B 6/022* (2013.01);
(Continued)

(58) Field of Classification Search
CPC .. A61B 6/485; A61B 6/487; A61B 2034/2065
See application file for complete search history.

(56) References Cited

U.S. PATENT DOCUMENTS 6,064,759 A * 5/2000 Buckley ............... G01B 11/024
348/125
6,493,575 B1 * 12/2002 Kesten .................. A61B 90/36
600/431
(Continued)

*Primary Examiner* — Jeffrey G Hoekstra
*Assistant Examiner* — Jason M Ip
(74) *Attorney, Agent, or Firm* — Jansson Munger McKinley & Kirby Ltd.

(57) ABSTRACT

A method for automatically determining the 3D position and orientation of a radio-opaque medical object in a living body using single-plane fluoroscopy comprising: (a) capturing a stream of digitized 2D images from a single-plane fluoroscope; (b) detecting an image of the medical object in a subset of the digital 2D images; (c) applying to the digital 2D images calculations which preserve original pixel intensity values and permit statistical calculations thereon, using (i) multiple sequential determinations of a midline of the medical object image, (ii) a plurality of unfiltered raw-data cross-sectional intensity profiles perpendicular to each sequentially-determined midline, (iii) removal of outlier profiles from each plurality of profiles, and (iv) statistically combining each plurality of profiles to estimate image dimensions; (d) applying conical projection and radial elongation corrections to the image measurements; and (e) calculating the 3D position and orientation of the medical object from the corrected 2D image measurements.

25 Claims, 24 Drawing Sheets

Related U.S. Application Data

(60) Provisional application No. 61/627,728, filed on Oct. 17, 2011, provisional application No. 61/573,557, filed on Sep. 8, 2011.

(51) Int. Cl.

| | | |
|---|---|---|
| *A61B 5/00* | (2006.01) | |
| *A61B 5/06* | (2006.01) | |
| *A61B 34/20* | (2016.01) | |
| *A61B 6/12* | (2006.01) | |
| *A61B 6/02* | (2006.01) | |
| *A61B 90/00* | (2016.01) | |

(52) U.S. Cl.
CPC .............. *A61B 6/12* (2013.01); *A61B 6/485* (2013.01); *A61B 6/487* (2013.01); *A61B 6/503* (2013.01); *A61B 6/5288* (2013.01); *A61B 6/582* (2013.01); *A61B 6/4441* (2013.01); *A61B 6/463* (2013.01); *A61B 6/5264* (2013.01); *A61B 2034/2065* (2016.02); *A61B 2090/367* (2016.02); *A61B 2090/376* (2016.02)

(56) References Cited

U.S. PATENT DOCUMENTS

| | | | |
|---|---|---|---|
| 6,549,648 B1* | 4/2003 | Rinn | G01B 11/024 382/151 |
| 7,457,458 B1* | 11/2008 | Daniel | H04N 5/21 348/E17.005 |
| 7,787,951 B1* | 8/2010 | Min | A61B 5/04012 607/17 |
| 2007/0122020 A1* | 5/2007 | Claus | A61B 6/583 382/131 |
| 2008/0031417 A1* | 2/2008 | Kramp | A61B 6/4441 378/95 |
| 2008/0095422 A1* | 4/2008 | Suri | G06K 9/6206 382/131 |

* cited by examiner

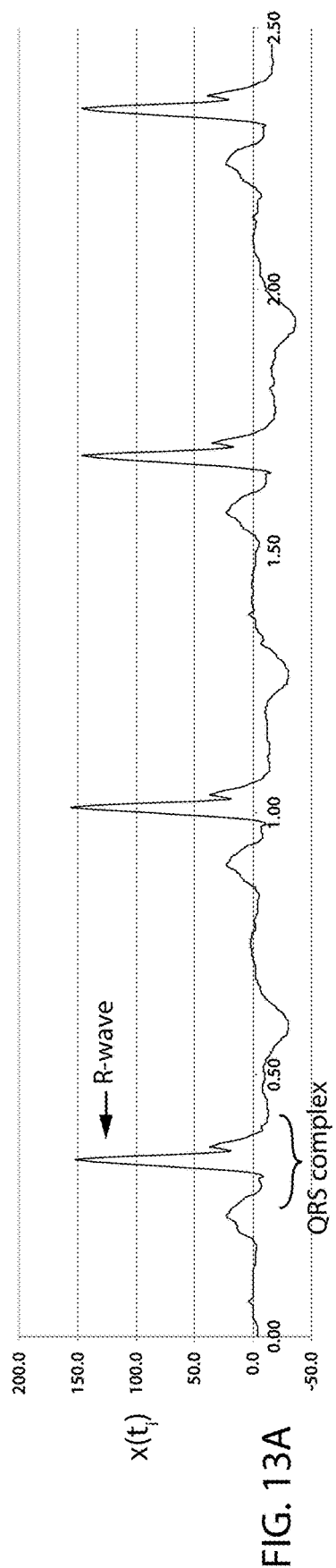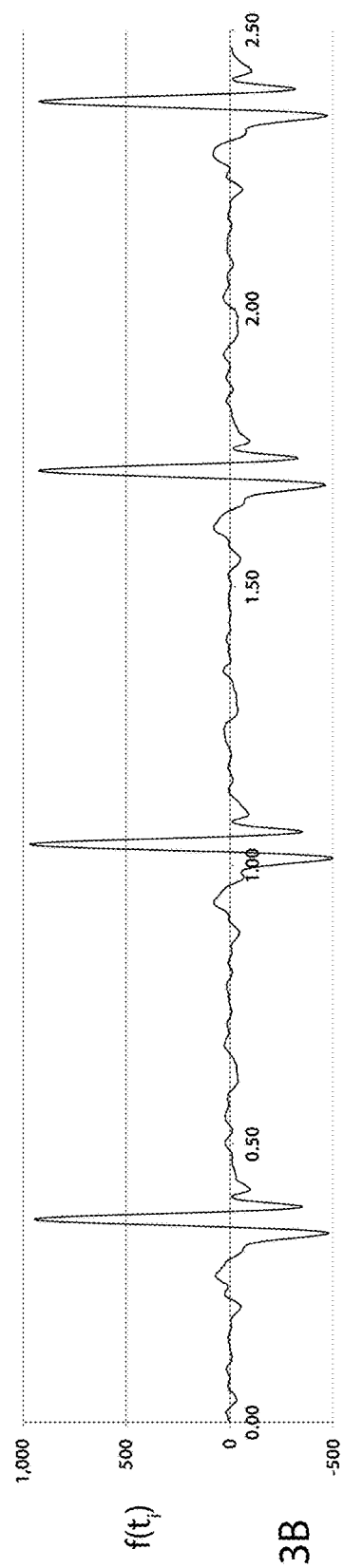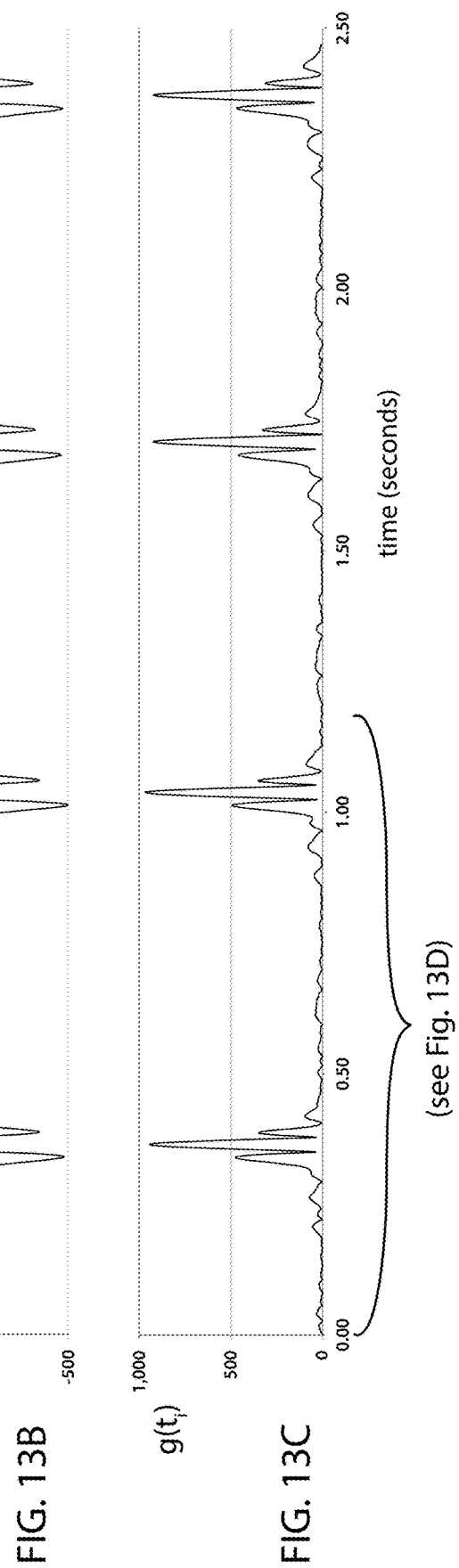
FIG. 13A
FIG. 13B
FIG. 13C

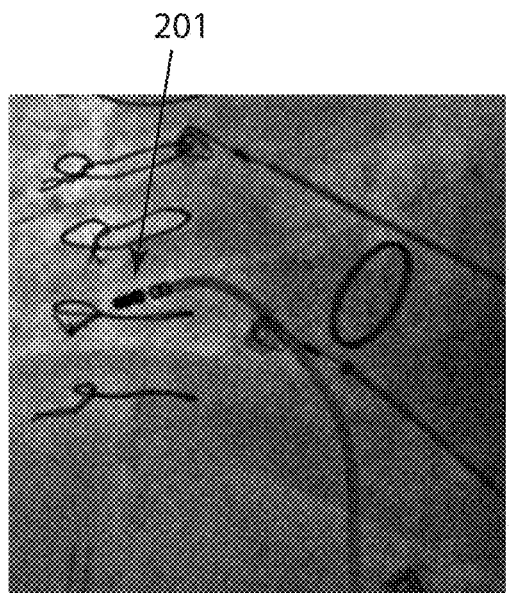
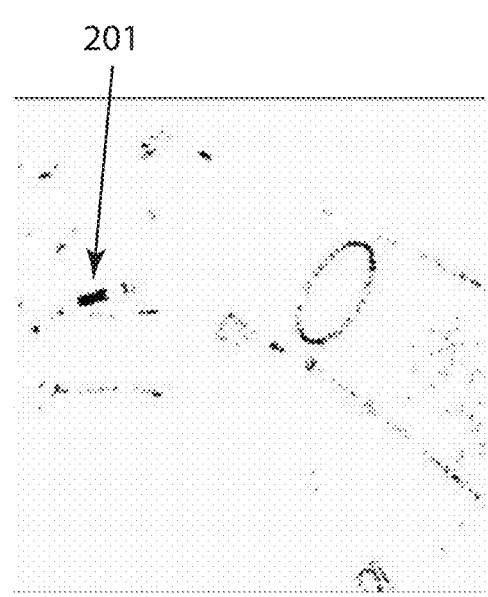
FIG. 16A  FIG. 16B
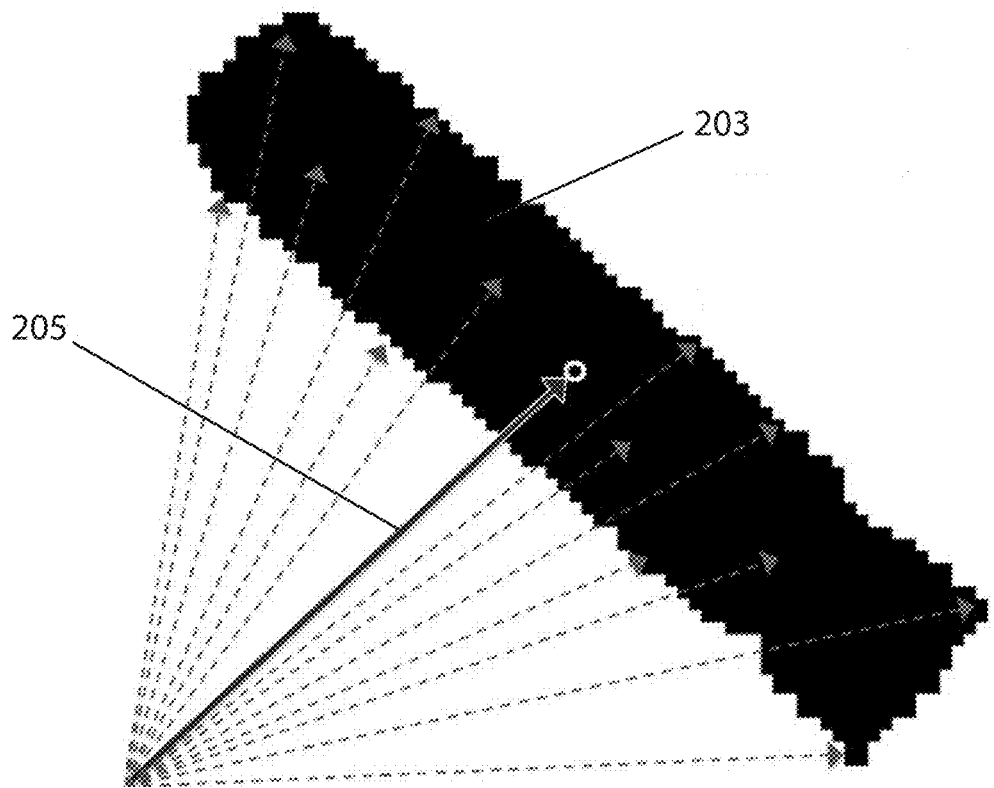
FIG. 17

AUTOMATICALLY DETERMINING 3D CATHETER LOCATION AND ORIENTATION USING 2D FLUOROSCOPY ONLY

RELATED APPLICATIONS

This application is a continuation of U.S. patent application Ser. No. 13/607,163 (Sra et al.), titled "Automatically Determining 3D Catheter Location and Orientation Using 2D Fluoroscopy Only" and published as US2013/0243153 and now U.S. Pat. No. 9,986,931. This present application claims the benefit of U.S. Provisional Application Nos. 61/573,557, filed on Sep. 8, 2011, and 61/627,728, filed on Oct. 17, 2011, the entire contents of which are incorporated herein.

FIELD OF THE INVENTION

The present invention generally relates to medical imaging systems and more particularly to 2D fluoroscopic systems for use during interventional medical procedures.

BACKGROUND OF THE INVENTION

Anatomical mapping systems provide the 3D position of a navigational catheter within the cardiac chamber of interest and, in some instances, can also be used to construct 3D maps of the cardiac chamber. These systems are, however, quite expensive to both acquire and operate. Therefore, these systems are available only in a few laboratories for use during interventional procedures, and some of these systems may require specifically-designed catheters such as catheters with built-in sensors.

Conventional fluoroscopy systems are available in all cardiac interventional labs for imaging and real-time navigation of catheters and other instruments and for the placement of leads and stents during interventional procedures. Other than the initial acquisition cost, such systems require little ongoing operation costs. Further, conventional fluoroscopic systems are able to visualize any type of catheter.

FIGS. 1A and 1B illustrate two examples of images obtained from a conventional fluoroscopic system during an atrial fibrillation ablation procedure. Shown in FIGS. 1A and 1B are a mapping and ablation catheter 2, an esophageal probe 3 which is placed inside the esophagus (posterior to the heart), a multi-electrode basket catheter 4, and a coronary sinus catheter 5. These catheters include radio-absorbing material and provide good image contrast compared to the biological tissue such as the lungs 6 and the cardiac silhouette 7. The attenuation of the X-ray beam in the lung is inferior to that of the heart because the lungs are filled with air, the density of which is less than regular anatomical tissue. There is no depth (z-axis) information of the different catheters discernible in these images despite the location of various structures and catheters in different orientations.

As illustrated in FIGS. 1A and 1B, fluoroscopy images produced by conventional systems have the limitation that they do not provide 3D image data. Biplane fluoroscopy (two 2D views from different directions) can be used to identify the relative position of an object such as a catheter. However, its usefulness is limited due to cost and to excessive radiation, and only 1 to 2% of interventional labs have the capability to perform biplane fluoroscopy.

FIG. 2 illustrates a conventional fluoroscopic system 10 used to acquire 2D fluoroscopic image data. The imaging process for conventional fluoroscopy involves an X-ray source 11 which sends an X-ray beam through a patient (not shown) on a table 12. X-ray generation is initiated by actuating a foot pedal 9 on a control panel 15 which is connected (connection not shown) to fluoroscopic system 10. An X-ray detector 13, which may be a flat-panel detector or an image intensifier/video camera assembly, receives the X-rays transmitted through the patient and converts the X-ray energy into an image. X-ray source 11 and X-ray detector 13 are mounted on opposite ends of a C-arm 8. Detector 13 performs the conversion using an X-ray detection layer that either produces light or releases electrons when stimulated by X-rays, and a light-to-electron conversion layer, e.g., photodiodes or electron collection layer, as appropriate, in which an electrical charge signal proportional to X-ray signal intensity in each picture element (pixel) is collected. Analog-to-digital conversion then produces a digital image. Whatever the X-ray detector, the resulting digital image is then processed, possibly stored, and displayed on a screen 14. A control panel is shown at 15. Images may then be displayed on computer display 14.

FIG. 3A illustrates a coordinate system for fluoroscopic system 10. The z-axis is defined from X-ray source 11 to the center of X-ray detector 13. X-ray (used interchangeably with fluoroscopy) table 12 defines an x-axis and a y-axis. The three axes are shown by the solid lines. The intersection of the axes is the center, or origin O, at (0,0,0) of the 3D space defined by axes x, y and z. Since C-arm 8 is able to move, the z-axis is defined herein when C-arm 8 is oriented in a vertical position as shown in FIG. 2, or a PA position (posterior-anterior position).

X-ray source 11 includes a cathode and an anode. Electrons interact with the anode material producing X-ray photons forming a cone-shaped beam. The beam is controlled by collimator blades to limit the patient's radiation exposure. The X-ray photons propagate in straight lines, forming an image on X-ray detector 13 at a precise location representing the matter encountered all along the ray that goes from the point of X-ray emission from source 11 to this location (pixel in the image) in detector 13. The intensity of the pixel is defined by the type and amount of material (tissue, contrast agent, interventional tool) encountered along this path. The attenuation of the X-ray beam varies as a function of the atomic number and the density of the traversed tissue. The current commercial standard for X-ray image resolution is about 0.2 mm×0.2 mm.

Fluoroscopic images, because they are projections, are representations of the imaged volume of 3D anatomy. This volume is transformed into a 2D projected image on X-ray detector 13 according to precise geometric rules based on the position of X-ray source 11, patient anatomy and detector position in the z direction (parallel to the central ray passing through center O). X-ray projection imaging thus embodies an inherent distortion due to the fact that X-ray source 11 is a finite distance from the anatomy being imaged. As a result, objects closer to X-ray source 11 are magnified in the detected image more than objects more distant from X-ray source 11, and there is no way to resolve these ambiguities without knowing the positions (or a priori sizes) of the objects of interest along the z-axis.

FIG. 3B is an illustration of the geometric magnification which results from the geometric arrangement and conic form of the output of the X-ray source 11 of the X-ray machine 10. FIG. 3B shows a simple 2D representation of the geometry of X-ray machine 10, including source 11, table 12 and detector 13. An object having width $w_o$ forms an image having an image width $w_i$ on detector 13. (For simplicity, such object and image are also referred to with reference identifiers $w_o$ and $w_i$, respectively.) Object $w_o$ is located at a distance SOD (source-to-object distance) from source 11, and detector 13 is located at a distance SID (source-to-image distance) from source 11. By simple geometry, the ratio of $w_i$ to $w_o$ is equal to the ratio of SID to SOD. Thus, the geometric magnification M of such an arrangement is M=SID/SOD.

In U.S. patent application Ser. No. 12/885,710, entitled "3D Model Creation of Anatomic Structures Using Single-Plane Fluoroscopy," an algorithm for estimating 3D coordinates of a point of interest such as a catheter tip using single-plane fluoroscopy is disclosed. The algorithm computes 3D position estimates by: (1) determining the 3D coordinates of an initial catheter-tip position; (2) advancing the catheter a small, measured amount and obtaining a fluoroscopic image; (3) measuring changes in the position of the catheter tip between the position in the image and the initial position of the catheter tip; (4) computing the actual (physical) changes in catheter-tip position in the x and y directions; (5) computing the 3D position of the catheter tip based on the geometry of the fluoroscopic system and changes in catheter-tip position in x and y; and (6) repeating these steps to generate a series of 3D positions of the catheter tip. This algorithm depends on knowledge of the initial 3D coordinates of the catheter tip and advancing the catheter by small, measurable amounts to be able to assume that the catheter tip moves in straight lines. This assumption permits the use of a linear distance formula to compute the 3D coordinates of successive point-of-interest locations. Initial phantom tests have suggested the existing algorithm is reasonable (error <8 mm) when the assumptions are met. However, in some scenarios, the restrictions on catheter advancement are too severe to be able to reduce 3D position errors.

A paper by Pascal Fallavollita entitled "Is Single-View Fluoroscopy Sufficient in Guiding Cardiac Ablation Procedures?" published in the International Journal of Biomedical Imaging, Vol. 2010, Article ID 631264, describes a system which uses X-ray system geometry and image filtering and pattern recognition techniques to estimate the depth (z-axis coordinate) of a catheter tip. The present invention is a significant improvement over the approach of Fallavollita, achieving increased accuracy and doing so in an automated fashion to avoid placing additional requirements on the clinician. The invention identifies the cues present within the fluoroscopic system and uses complex computational algorithms to identify the 3D location of the catheter. Pixel values in fluoroscopic images are affected by out-of-plane angle, depth, and distance from the central ray, and these and other characteristics are taken into account to identify more precise estimates of 3D locations of the catheter tip. With 3D locations of catheter tips determined, various 3D maps such as activation and voltage are created.

It is desired that for a method to be useful, the z-coordinate accuracy of a method of determining 3D coordinates in a fluoroscopic environment should achieve depth (z-coordinate) accuracy of ±4 mm. At least such accuracy is desirable since, for example, a typical lesion formed by a cardiac ablation catheter may be about 4-6 mm in diameter; thus positioning accuracy on that order is desirable for the inventive method to be useful during such interventional procedures.

OBJECTS OF THE INVENTION

It is an object of the present invention to provide a set of digital image processing techniques and mathematical algorithms for the purpose of reconstructing the 3D location and spatial orientation of a radio-opaque medical object from 2D (single-plane) digitized fluoroscopic images. One specific object of the present invention is to provide such a system in which the radio-opaque medical object is a cardiac mapping and ablation catheter or other object used in cardiac imaging or intervention.

Another object of the present invention is to provide a medical imaging system which reconstructs the position and orientation of a radio-opaque medical object and generates three-dimensional models of anatomical structures using readily-available medical equipment.

Another object is to provide such a system using algorithms which take into account the inherent limitations and properties of the 2D fluoroscopy system.

Yet another object of the present invention is to provide a medical imaging system which improves the accuracy and therefore the effectiveness of medical procedures by using gated images to minimize the effect of motion during operation.

Another object of the present invention is to provide such a system which operates automatically and in real time so that it can be used contemporaneously with interventional procedures.

Still another object of the present invention is to provide such a system with sub-pixel image measurement accuracy, thereby achieving useful z-coordinate accuracy at an economical level not available with other systems.

Yet another object of the present invention is to provide a system for determining the 3D position and orientation of a radio-opaque medical object in a living body using single-plane fluoroscopy which is independent of 2D fluoroscopic hardware being used.

These and other objects of the invention will be apparent from the following descriptions and from the drawings.

SUMMARY OF THE INVENTION

The present invention is a method for automatically determining the 3D position and orientation of a radio-opaque medical object in a living body using single-plane fluoroscopy. The method includes: (1) capturing a stream of digitized 2D images from a single-plane fluoroscope; (2) detecting an image of the medical object in a subset of the digital 2D images; (3) applying to the digital 2D images calculations which preserve original pixel intensity values and permit statistical calculations thereon, using (i) multiple sequential determinations of a midline of the medical object image, (ii) a plurality of unfiltered raw-data cross-sectional intensity profiles perpendicular to each sequentially-determined midline, (iii) removal of outlier profiles from each plurality of profiles, and (iv) statistically combining each plurality of profiles to estimate image dimensions, thereby to measure the medical-object image from a final estimation of image dimensions; (4) applying conical projection and radial elongation corrections to the image measurements; and (5) calculating the 3D position and orientation of the medical object from the corrected 2D image measurements.

It will be helpful in understanding the present invention to lay out definitions of certain terms used herein.

The term "radio-opaque medical object" as used herein refers to various medical instruments, tools, inserts, and the like such as catheter tips, pacemaker and defibrillator leads, stents, identifiable portions of larger medical objects, and the like which are substantially radio-opaque and have fixed dimensions. Most of this document describes the present invention in the context of determining location and orientation of a cardiac catheter tip. However, this embodiment is not intended to be limiting; the invention is applicable to a wide variety of radio-opaque medical objects, and the specific lists of object types and example objects are also not intended to be limiting. The term "radio-opaque medical object" is sometimes shortened herein as "medical object."

As used herein, the term "single-plane fluoroscopy" refers to operation of a fluoroscopy system at a fixed angle at which all images are taken during a procedure. The present invention is a method for the 3D determination of the positions and orientations of a catheter as it is moved within a region of the human body, such as a cardiac chamber. Although the present invention involves only one fixed angle to be used to create images, as described later in this document, the invention may include two views for independent assessment of depth for initialization.

The term "two-view fluoroscopic measurement" as used herein refers to 3D position determination using two fluoroscopic images taken at different angles of the C-arm.

The term "forming clusters of image pixels" as used herein refers to the process by which pixels in an image are grouped together or associated with one another as possible images of a medical object being sensed.

The term "pixel-level geometric calculations" as used herein refers to calculations which preserve the original pixel-intensity values and permit statistical calculations to be performed on the pixel intensity values. Pixel-level geometric calculations are described in more detail later in this document.

The term "effective X-ray dimensions" as used herein refers to dimensions which are measured in a consistent fashion such that even if the dimensions are not equivalent to the actual physical dimensions of the radio-opaque medical object being measured, the effective dimensions are consistently sensed and therefore can be relied upon in the measurement process. Further discussion of effective X-ray dimensions is included below in this document.

The term "keystoning" as used herein refers to the variations in image width due to out-of-plane orientation angle.

The term "refractory count" as used herein refers to a count that corresponds to a time period. No limitation is intended as to how the time period is determined, i.e., it does not have to be determined by a counter.

The term "trigger-window filter" as used herein refers to a process by which inputs to such filter are ignored during a particular time window (lockout period) based on other inputs received by the filter.

The term "OR-gate" as used herein refers to a device or process which performs the logical OR operation. Such operation is well known to those skilled in the art of instrumentation.

The terms "location" and "position" are used interchangeably herein to refer to the 3D coordinates of an object such as a catheter tip or other imaged structures.

In preferred embodiments, the method further comprises initialization steps before the detecting step, the initialization steps determining the effective dimensions of the medical-object image and setting medical-object image size-limit criteria.

In some preferred embodiments, with respect to each 2D image in the subset, the detecting step includes applying a threshold filter to the 2D image, forming clusters of image pixels, evaluating each of the clusters against the medical-object image size-limit criteria, and selecting the cluster that contains the image of the medical object. Some of these embodiments further include computing center, longitudinal midline and bounding-box data of the selected cluster.

In some preferred embodiments, the inventive method further includes applying the center, midline and bounding-box data to the unfiltered 2D image, expanding the bounding box area around the medical-object image, and up-sampling such 2D image. In some of these embodiments, the up-sampling is performed only along each cross-sectional image profile.

In some preferred embodiments, the method further includes identifying medical-object image edges by selecting edge points on each profile at a fixed percentage of profile intensity range. In some of these embodiments, the profile intensity range of a profile is the difference between the maximum and minimum intensity values for such profile.

In some highly preferred embodiments of the inventive method, identifying medical-object image edges includes computing least-squares-fit representations of the edges.

In some highly-preferred embodiments, the measuring step further includes recomputing the medical-object image center based on the least-squares-fit edges and determining medical-object image width, length and keystoning in the 2D image.

In some preferred embodiments, the method further includes forming a plurality of cross-sectional image profiles parallel to the midline and identifying medical-object edges substantially perpendicular to the midline.

In some highly-preferred embodiments, the measuring step further includes recomputing the medical-object image center based on the least-squares-fit edges and determining medical-object image width, length and keystoning in the 2D image.

In some embodiments, the subset of 2D images is selected by respiration gating from a respiration signal from the living body, and in some embodiments, the subset of 2D images is selected by cardiac gating from an ECG signal from the living body.

In highly-preferred embodiments, the method further includes creating a 3D map of an anatomical structure within the living body. In some of these embodiments, the anatomical structure is a cardiac structure.

Some highly-preferred embodiments of the inventive method include the step of displaying the 3D map on a display device, and some highly-preferred embodiments include displaying the 3D position and orientation on the display device.

In some embodiments, the step of applying measurement corrections includes correcting medical-object image measurements for out-of-plane angle.

Some highly-preferred embodiments of the inventive method include the steps of capturing, detecting, applying geometric calculations, applying corrections, and calculating 3D position and orientation multiple times with the medical object in a single position and averaging the calculated 3D position and orientation data, thereby to enhance accuracy of the determination.

DESCRIPTION OF THE DRAWINGS

FIG. 9 is a detailed schematic description of an embodiment of the method or process of sub-pixel statistical edge detection of a catheter-tip image.

FIG. 13A is a 4-heartbeat portion of an example digitized channel ECG signal $x(t_i)$.

FIG. 13B is an example portion of an intermediate digital ECG signal $f(t_i)$ generated by filtering $x(t_i)$ from FIG. 13A with a bandpass filter.

FIG. 13C is an example portion of a filtered ECG signal $g(t_i)$ generated by filtering $f(t_i)$ from FIG. 13B with an absolute value filter.

FIG. 16A is an example 2D X-ray image of a number of objects in a living body, including a cardiac catheter.

FIG. 16B is an image created by applying a threshold filter to the example image of FIG. 16A.

FIG. 17 illustrates one embodiment of a method to compute the center of a cluster of pixels in a thresholded image.

FIG. 19A illustrates the case in which the image cluster is generally along the x-axis. FIG. 19B illustrates the case in which the image cluster is generally along the y-axis.

DETAILED DESCRIPTION OF PREFERRED EMBODIMENTS

Single-plane fluoroscopy offers a 2D animated view of a patient to a physician during operations involving catheters and leads. Using such a system, despite a physician's experience, the position of the patient, and the relative position of the catheter to anatomical features, an imprecise 3D position of a catheter is determined. This invention details the use of image analysis algorithms to identify the location of the catheter tip in 3D space using only 2D fluoroscopy. (Although any radio-opaque instrument can be used, the embodiments presented herein utilize cardiac catheter tips as the points-of-interest for 3D position estimation.)

As mentioned above, it is desirable to achieve z-coordinate determination accuracy of at least ±4 mm. In order to achieve such accuracy, it has been determined that the precision required in measuring medical-object dimensions is about 0.023 mm (for a typical catheter size and detector geometry). Since the inventive method disclosed herein estimates object dimensions using two edges formed from a series of edge points, the error required for each point is half of this (0.023 mm/2=0.011 mm). For a typical detector with resolution of 1000×1000 pixels and an area of 20×20 cm, each pixel is 200 mm/1000 pixels=0.2 mm/pixel. The fraction of a pixel corresponding to a precision of 0.011 mm is 0.011/0.2=0.05 pixels (about ½0th of a pixel).

Figure 4:
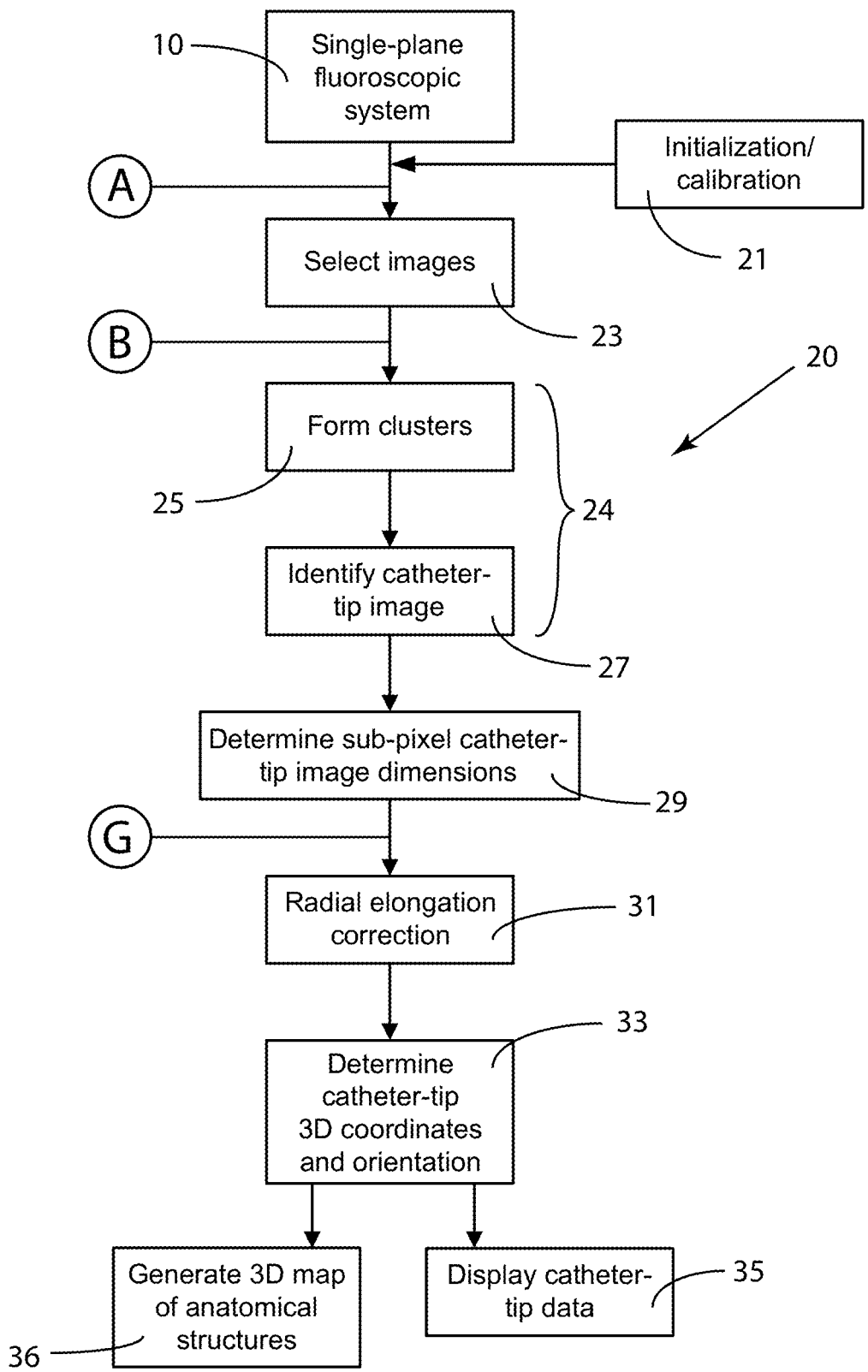
FIG. 4 is a general schematic of an embodiment of the inventive method for determining the 3D location of an object such as a catheter using a single-plane fluoroscopic system.

FIG. 4 is a general schematic of an embodiment 20 of the inventive method for determining the 3D location of an object such as a catheter using a single-plane fluoroscopic system. For convenience, the inventive system henceforth is called the Catheter Tip 3D Location System and will be referred to herein as C3DLS to shorten the terminology. The term "system" is used to describe the method since the method is carried out primarily by software which constitutes a system in the wider use of the term. The terms "process" and "functional element" as well as the specific terms referred to in the various elements in the schematic figures are used interchangeably herein in describing the operations or method steps of the inventive method or system.

C3DLS 20 includes the use of a conventional single-plane fluoroscopic system 10 which generates a series of sequential 2D fluoroscopic images which are available as a stream of digital images. The rate at which such images are generated may be a typical rate such as 7.5 or 15 images (or frames) per second but such rates are not intended to be limiting to the scope of this invention. (X-ray systems are capable of generating both lower and higher rates of images per second.) Images in such stream are available to be processed by C3DLS and are selected by an image selection process in functional element 23. Further detail for the image selection process of element 23 is found in FIG. 6 and described later in this document. Image selection process 23 determines which images will be processed by C3DLS 20.

Exemplary images are a 1000×1000 array of 8-bit bytes, one byte per pixel with each byte holding an intensity value ranging from 0 to 255. Another example is a 512×512 array of 12-bit pixel intensity values ranging from 0 to 4095 with two bytes (16 bits) representing each pixel. The left/right angulation and cranial/caudal angles are also needed and input for each image frame. These examples are not intended to be limiting; other data formats are possible.

The remainder of C3DLS 20 includes the processing of the images which have been selected by image selection process 23. A starting point for these processing steps is labeled as point B in FIG. 4 in order that such point may be understood in subsequent figures. The same is true for points A-G in FIGS. 4 through 9.

Figure 7:
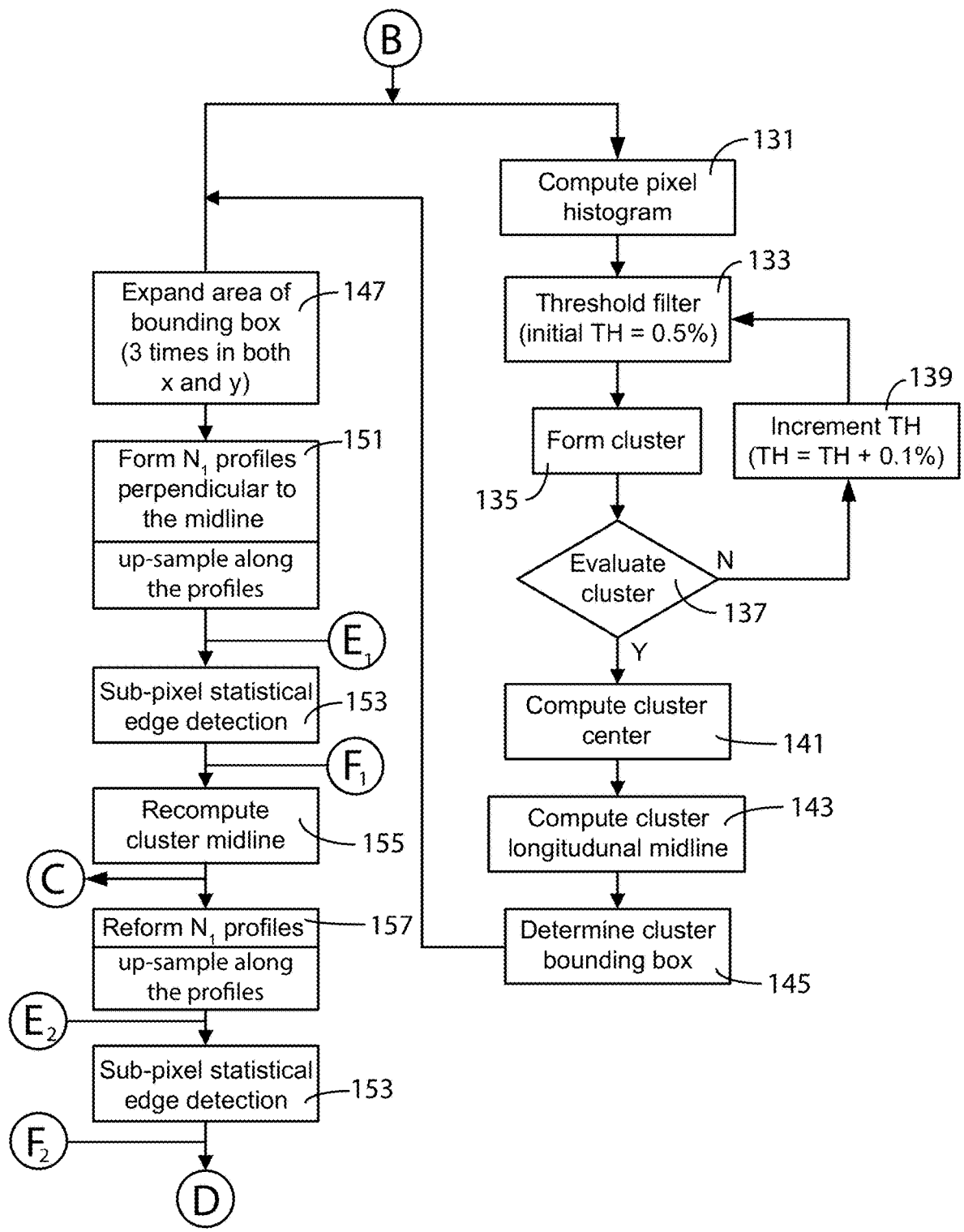
FIGS. 7, 8 and 9 together present a detailed schematic description of many of the functional elements of the general schematic of FIG. 4, beginning with the formation of image clusters in order to locate candidate catheter-tip images and through the process of applying corrections to catheter-tip measurements.

C3DLS 20 includes an automated process by which a catheter tip is found and identified as a catheter tip within images which have been selected by image selection process 23; this process 24 (indicated by brackets) includes two functional elements, shown in C3DLS 20 as cluster formation 25 and catheter-tip identification 27 and is described in more detail with respect to FIG. 7, generally with functional blocks 131-145. Cluster formation 25 is a process by which pixels which are neighbors in an image are associated with one another as possible groups which represent an object of interest. Objects which may be catheter tips form such groups (clusters) within an image. Catheter-tip identification 27 is the process by which the appropriate clusters are determined to be images of a catheter tip.

C3DLS 20 includes measurement of a catheter tip in functional element 29 and further refinement of such measurement in functional element 31. Correction 31 of a catheter-tip measurement involves several inventive steps and represents another important concept in the present invention. Further details are presented later in this application with respect to FIG. 7-9, beginning with functional blocks 147 of FIG. 7 and including all of FIGS. 8 and 9.

C3DLS 20 then proceeds in functional element 33 to determine the 3D coordinates and orientation of a catheter tip based on the accurate measurements of the catheter tip, using the geometry of fluoroscopic system 10 in this determination.

With the 3D position and orientation of the catheter tip now known, such information is available to the clinician to be used in a variety of ways. Functional element 35 represents the display of such data in a variety of ways, among which are a simple coordinate display which shows the depth (z-coordinate) of the catheter tip so that the clinician can be aware of depth while viewing x and y image information. However, many other ways to present such data may also be used, including the generation and display of 3D mapping data to enable the clinician to visualize various anatomical structures in order to assist in an interventional procedure.

The following sections describe C3DLS 20 in more detail. Among the concepts involved in the present invention, the invention takes into account the inherent characteristics of 2D fluoroscopy images and uses sophisticated computational algorithms to resolve the issue of catheter depth (z-coordinate) in 3D space, data which is missing in conventional X-ray systems.

Fluoroscopic images, because they are projections, are representations of an imaged volume in which the imaged 3D anatomy is transformed into a 2D projected image according to precise geometric rules based on the relative positions of the X-ray source 11, the anatomy being imaged, and X-ray detector 13. X-ray projection imaging thus includes an inherent projection distortion due to the fact that X-ray source 11 is at finite distance from the anatomy being imaged on table 12. As a result, objects closer to source 11 are magnified more than objects more distant from source 11 in the projected image.

Figure 10:
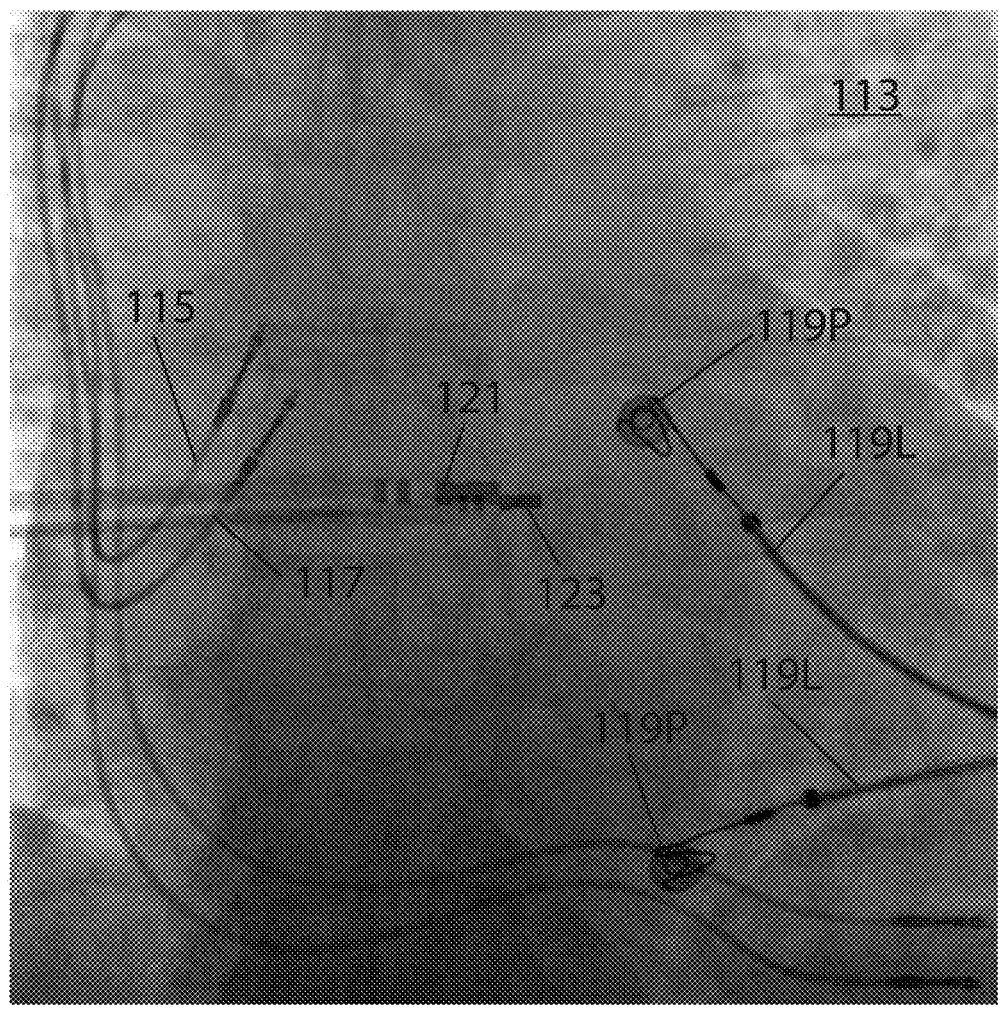
FIG. 10 is a fluoroscopic image illustrating the effect of fluoroscopic system geometry on image size.
Figure 11:
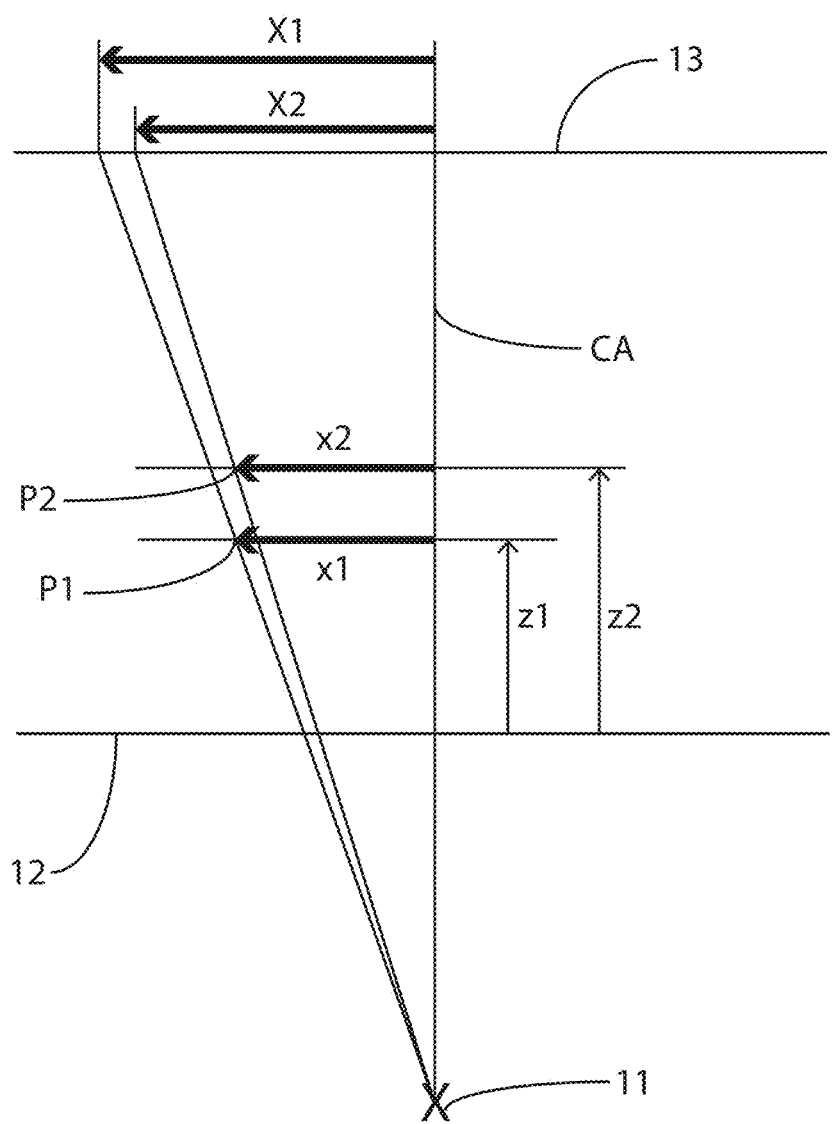
FIG. 11 is a diagram illustrating the effect of fluoroscopic system geometry on image size.

FIGS. 10 and 11 depict such a conic projection of fluoroscopy system 10 and the images obtained therefrom. FIG. 10 shows a fluoroscopic image 113 with permanent pacemaker leads 115 and 117. Two ECG patches 119P and accompanying leads 119L are shown in image 113. There is no difference in the sizes of the two patches 119P and leads 119L since they are located in the same z position. However, two catheters 121 and 123 are also shown in image 113. Catheters 121 and 123 are identical catheters, but catheter 121 appears in image 113 as larger than catheter 123 since catheter 121 is located posterior to the patient's chest and catheter 123 is located anterior to the chest. Catheter 121 is therefore closer to the X-ray source and therefore the magnifications of the images of catheters 121 and 123 differ due to the conic projection or keystoning effect present from the geometry of fluoroscopic system 10.

FIG. 11 provides further illustration, depicting a diagrammatic representation of the images produced by the effect of conic projection. X-rays emanate in a conical beam from X-ray source 11 through which a central axis CA passes. Two points P1 and P2 are located at distances x1 and x2, respectively, from central axis CA of 2D fluoroscopic system 10. x1 and x2 are equal distances from central axis CA. P1 and P2 are also located at distances z1 and z2, respectively, from patient table 12. In this example, although x1 and x2 are equal, the x-positions of the corresponding points in the image on X-ray detector 13, X1 and X2, are different. X1 is larger than X2, and this difference is illustrative of the distortion in 2D fluoroscopic images.

Those X-rays in the conical beam that do not undergo photoelectric absorption or Compton scatter in the target object (e.g., a human body) reach detector 13 to form the primary 2D radiation image. The primary image information in the spatial pattern of the X-ray photons that reach detector 13 results from the differential, incremental attenuations presented by each layer, structure, and device within the patient, e.g., lung, heart, vertebrae, catheters, as the primary X-rays travel along their straight-line paths. The attenuation follows the well-known exponential attenuation process. In addition, some of the Compton scatter generated as the primary X-rays pass through the patient also reach detector 13. These X-rays carry no practical information, reduce the apparent contrast of objects within the anatomy, and add to the quantum X-ray noise in the image.

X-ray detector 13 converts the spatial pattern of the X-rays incident upon it into a digital image. This digital image is typically processed, stored, and displayed. In addition, the information in the digital image is used to control an X-ray generator which in turn energizes an X-ray tube. Typically, fluoroscopic system 10 includes an automatic brightness control (ABC) which is used to control system 10 to scale the digital image such that the average intensity of the digital image will be around or slightly lower than 50% of the digital image intensity scale, e.g., an average intensity of 100 within a detector range of 0 to 255 (an 8-bit image intensity scale). Intensity values in the area of the heart might be around 100, the values in the lung well over 200, and the values in the spine around 25. Intensity values in an image of a catheter electrode tip may be close to 0 or a bit higher, depending on the beam spectrum and the amount of scatter in the image.

In general, the higher the intensity level of the image, the higher the image quality, due to a higher signal-to-noise ratio (SNR). However, all other things being equal, the higher the image SNR, the higher the radiation dose to the patient. So each imaging mode of the X-ray system presents a compromise between image quality (SNR) and patient dose. Due to the amount of fluoroscopy time required for complex cardiac interventional procedures, clinicians operate at the lowest patient dose and image SNR levels that provide adequate imaging. This in turn means that the typical fluoroscopic image is "noisy," meaning that there are significant statistical variations in the intensity levels in each picture element (pixel) due to random X-ray quantum noise.

The factors that fluoroscopic system 10 may control include the beam energy spectrum, the beam intensity (for a given beam spectrum), and the exposure time. An operator of system 10 typically has the ability to select the fluoroscopic imaging rate, measured in number of images per second. For the cardiac applications encompassed by this invention, useful rates may typically range from 3.75 to 30 images per second. The degree of attenuation presented by each type of body tissue and devices placed within the patient is determined by the tissue or material composition, its density, and the X-ray beam spectrum. Since the X-ray system automatically adjusts the beam spectrum, among other factors, to achieve the desired image SNR, it follows that the attenuation of a device placed within the body, and therefore its contrast relative to adjacent areas in the image, will vary depending on the size of the patient, the particular imaging scene, and various settings of system 10. The amount of X-ray scatter in the image scene, which is dependent on patient size, imaging field-of-view, distance of the patient from detector 13, and other factors, also influences the contrast of devices imaged within the body.

Figures 1A, 1B:
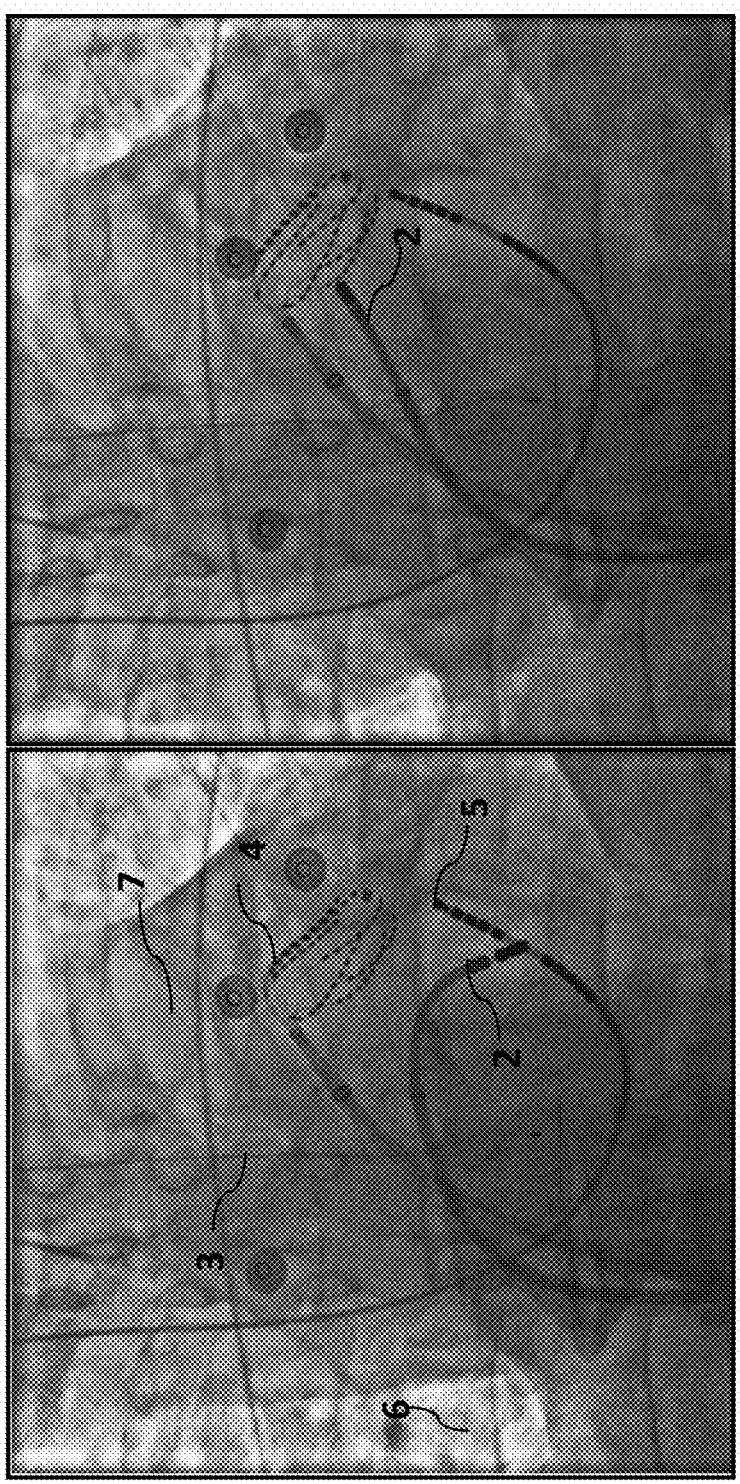
FIGS. 1A and 1B are two exemplary 2D X-ray images from a cardiac interventional procedure showing multiple catheters and certain anatomical structures.
Figure 2:
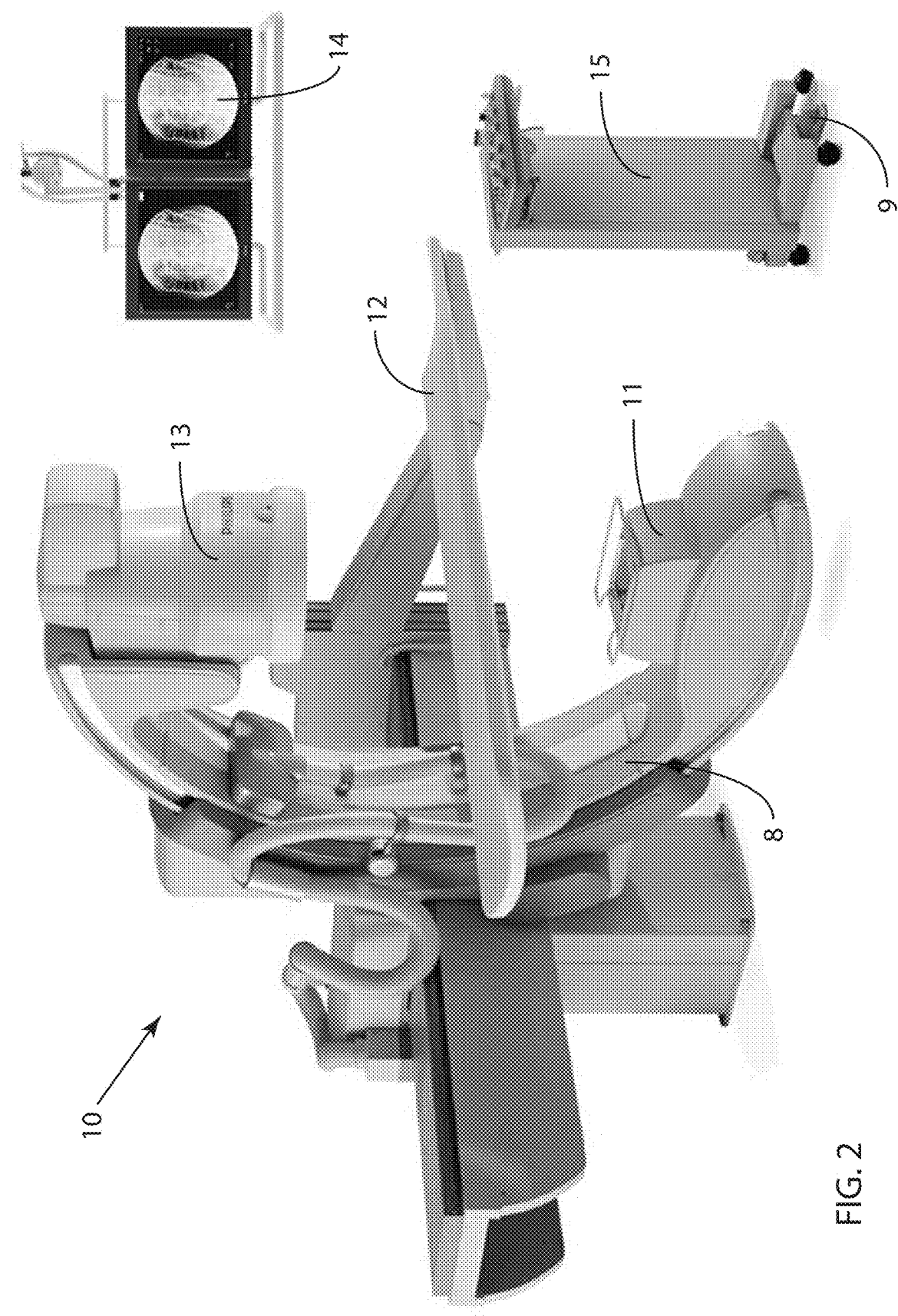
FIG. 2 is an illustration of a conventional X-ray machine with the C-arm in the anterior-posterior image acquisition position.
Figure 3A:
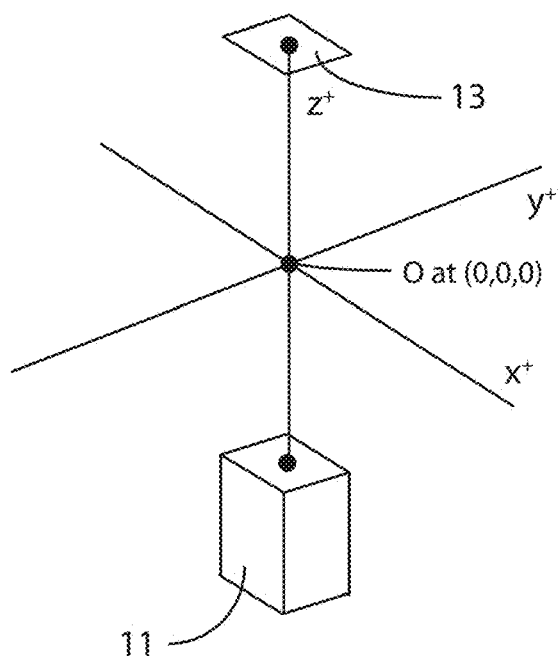
FIG. 3A illustrates the set of axes which define the 3D coordinates of a procedural suite. Each element of the suite has a position which can be described by coordinates in this coordinate system.
Figure 3B:
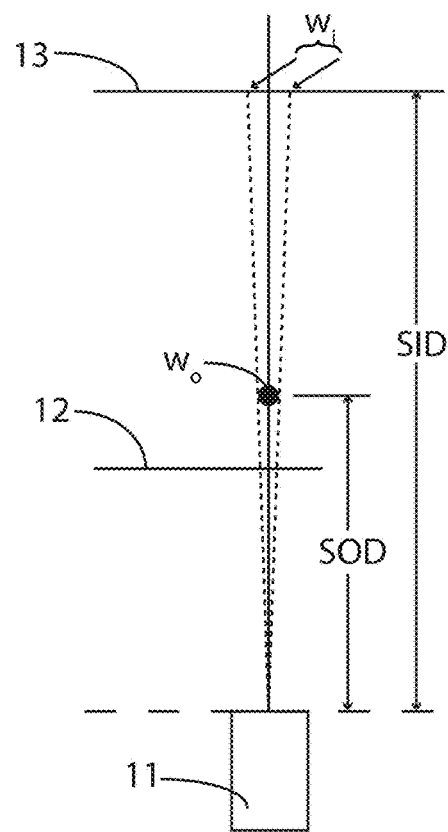
FIG. 3B is an illustration of the geometric magnification which results from the geometric arrangement and conic form of the output of the X-ray source of the X-ray machine of FIG. 2.
Figure 5:
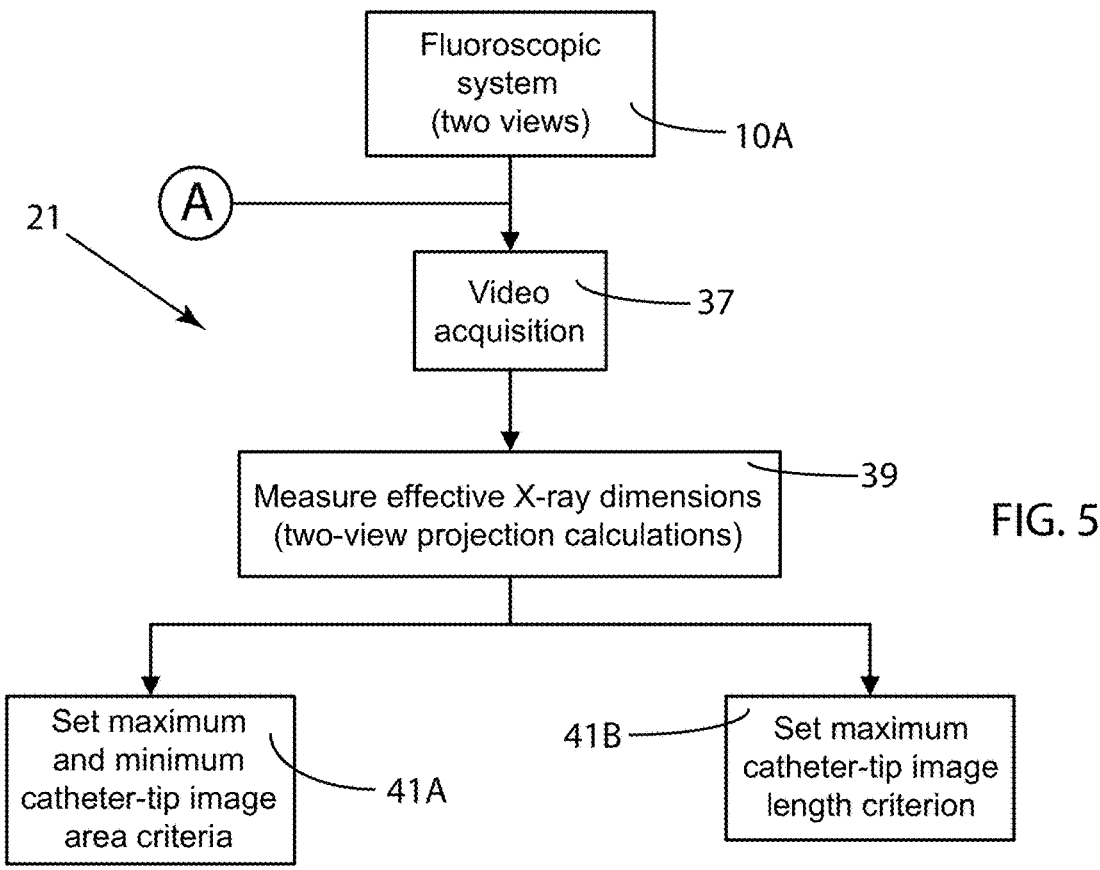
FIG. 5 is a schematic description of the initialization and calibration processes of the method of FIG. 4.

Referring again to FIG. 4, functional element 21 includes steps which initialize and calibrate C3DLS 20. FIG. 5 is a more detailed schematic representation of the initialization and calibration steps 21. FIG. 5 includes fluoroscopic system 10A, labeled with reference number 10A instead of 10 to indicate that single-plane fluoroscopic system 10 is used during initialization and calibration steps in two different C-arm 8 angular positions in order to generate two 2D X-ray images to capture z-coordinate information. (The term "two-view fluoroscopy" is used to differentiate it from biplane fluoroscopy in which additional hardware is involved in order to generate the second 2D X-ray image in a plane different from the first plane at the same instant the first image is generated.) An important object of the present invention is to provide 3D position and orientation information using the simplest of fluoroscopic system hardware (e.g., system 10 in FIG. 2). Two-view fluoroscopy refers to the process of first generating a 2D X-ray image in a first C-arm 8 angular position and then generating a second 2D X-ray image (of the same objects in the same position) after rotating C-arm 8 of conventional single-plane fluoroscopic system 10 into a second angular position. An image selection process 23 serves to capture and select specific images as desired during initialization and calibration. Image selection 23 is controlled either automatically or manually to supply the desired digital images for processing by C3DLS 20.

In order to initialize and calibrate C3DLS 20, the effective X-ray dimensions of a catheter tip are measured using two-view fluoroscopy, shown in FIG. 5 as functional element 39 (two-view projection calculations). Determination of effective X-ray dimensions is an important step in C3DLS 20. Catheters may be coated with a layer of resilient material which both varies in thickness from catheter-to-catheter and may not have the same ability to absorb X-ray energy as other parts of a catheter (e.g., metallic parts). This, together with the existence of catheter manufacturing process variations, means that (1) an assumption cannot be made as to actual catheter dimensions (e.g., diameter) based on manufacturer model number and (2) a physical caliper measurement is inadequate to characterize how a particular catheter will appear in an X-ray image.

The measurements of functional element 39 are performed by placing a catheter on table 12 (e.g., on top of the patient or directly on table 12 in its sterile package) between X-ray source 11 and X-ray detector 13, and two images from different known C-arm 8 angular positions and geometry are acquired by video acquisition in functional block 37. The analytic methods to determine the 3D coordinates and the effective dimensions of a catheter using data from two 2D images of the same object taken from two different angles are well known to those skilled in the art of mathematics, involving an over-determined system of three equations with two-unknowns. One such method utilizes the method of least squares. In general, the points of intersection (x,y,z) will not be precisely the same because of pixelation within the images. Thus, such statistical methods are applicable.

In order for such analysis to provide accurate estimates of effective X-ray dimensions, the points (x,y,z) of the catheter tip identified within the two images must correlate with the same point physically on the catheter; otherwise the assumption behind the analysis is incorrect and will lead to erroneous results. It has been found that the center of the generally rectangular area of a catheter-tip image and the four corners of such area are good points for such determinations.

Catheter diameters are important dimensions which are used within C3DLS 20. The effective X-ray diameter is the value of catheter-tip diameter that, when applied to the depth calculations made from measured catheter-tip image diameters in 2D fluoroscopic images, provides the most accurate, unbiased results. Use of the effective X-ray dimensions significantly reduces measurement bias because their determination is calculated using the same measurement biases that will occur in subsequent single-view measurements. Since the geometric magnification factor involved in each of the two views is known, either view can be used to calculate the effective X-ray diameter, or for increased accuracy, an average of two or more values may be used.

The measurement of a catheter tip from a 2D image is subject to biases from several sources, including X-ray tube focal spot penumbra, image processing (e.g., edge enhancement), and the choice of threshold value applied to the intensity profile of the catheter tip in the image. The focal spot penumbra, for example, blurs the edges of the catheter tip, making it more difficult to define the exact edges. X-ray detector 13 introduces some blurring of the catheter-tip image edge due to lateral dispersion of signals within detector 13 and the fact that the detector elements are of finite size (e.g., 140-200 microns). Further, a threshold value is used to make an estimate of the location of the edges of the catheter tip within the image. This threshold value is an intensity value between the dark area of the catheter-tip image and the lighter background area around the dark image. The particular threshold value is chosen to be not overly sensitive to background noise but may be a source of error.

These biases are present in the measurements made at known catheter-tip depth with the two-view images but are also present in all other subsequent catheter-tip width measurements as the C3DLS process proceeds, so the subsequent measurement biases tend to be canceled out by using the effective X-ray dimensions. For example, any measurements of a catheter made at the same depth as the two-view images should be the same, with no bias. Further, biases should not vary significantly over the range of depths that are likely to be encountered in navigating within the heart or other organs in the body using C3DLS 20. In interventional electro-physiology procedures, the movements of the catheter tip may be in the range of ±3 cm from its initial depth. Since the source 11-to-image 13 distance is typically in the range of 100-120 cm, the range of depth excursion is relatively small.

The process 39 of determinating effective X-ray dimensions of a catheter tip also includes the identification of the catheter-tip image within the two images. Such identification may be done with user interaction or by automatic identification steps. Such automated steps are described later in this document as steps within the C3DLS process and are applied within initialization and calibration as needed. Since automation is a major object of the present invention, automatic catheter-tip image identification is the preferred approach within initialization and calibration.

Other steps within initialization and calibration include setting criteria for maximum and minimum catheter-tip image area (step 41A) and setting a criterion for a maximum catheter-tip image length (step 41B). Each of these quantities and relationships is used later on in the calculations carried out within C3DLS 20 and will be discussed later in this document.

Although any or all sequentially-obtained images can be analyzed and used, an important part of the C3DLS process is the selection of which image frames are processed by the algorithms within C3DLS 20. Not all images are processed because of (1) physical movement of the patient (e.g., cyclical cardiac and respiratory movements and other motion such as patient or equipment repositioning) and (2) the processing speed of the computer. For cyclical motion, it is desirable that images processed within C3DLS 20 are captured at the same phase within these motions and that the computational results of C3RDS 20 are displayed in real-time to the clinician. In order to select images at the same phase within these movements, processes by which images are selected during periods of relatively small motion may be employed. Such processes are known as gating.

Referring again to FIG. 4, each 2D image which is processed by C3DLS 20 after the initialization and calibration 21 is selected from the sequential stream of digital images input to functional element 23. The stream of digital images may be generated by a number of different hardware configurations and is represented as video acquisition 37. One object of the present invention is to provide a system which can be used with a wide variety of conventional 2D X-ray machines, the video output of which may vary considerably. One way to satisfy this need is to acquire digital images from the signals which are used to drive the displays of the X-ray images. Such approaches are well known to those skilled in the art of computer and imaging hardware.

Figure 6:
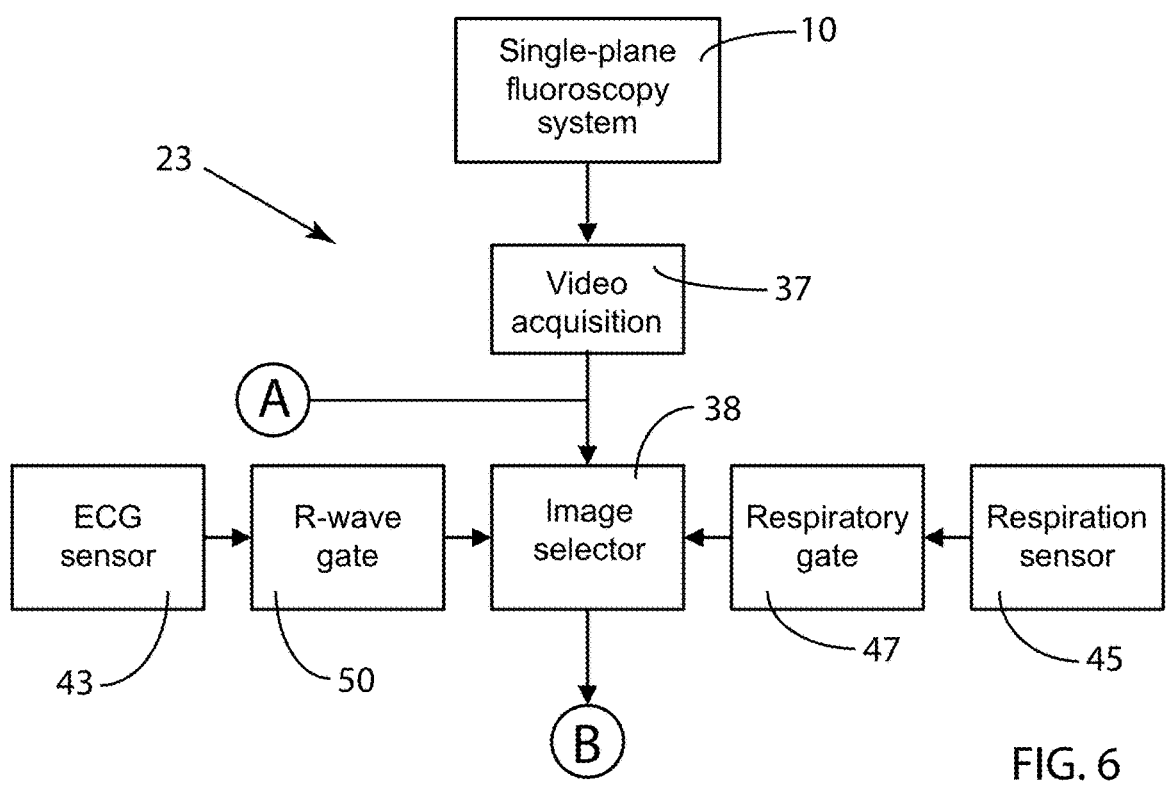
FIG. 6 is a schematic description of the image selection process of the method of FIG. 4.

FIG. 6 illustrates the image selection process. C3DLS 20 includes two subsystems which are configured to select images to be processed, a cardiac-based system (an ECG sensor 43 and an R-wave gate 50) and a respiration-based system (a respiration sensor 45 and a respiratory gate 47). One or both such systems may be used to control image selector 38. Other possible approaches to image selection other than cardiac gating and respiration gating may be programmed into image selector 38. These may include but not be limited to timing based on another signal or input command available.

Both cardiac and respiration gating are used to select images during which minimal motion occurs in order to minimize image blurring which results from movement during X-ray detection. In the case of cardiac gating, it may also be desirable to select images during a particular phase of the cardiac cycle.

In the following section, R-wave gating, the process by which fluoroscopic images are ECG-gated, is described.

The human heart is composed of electrically-active muscle cells. These cells contract when the cell membranes depolarize, and this results in (1) the vital contraction of the four chambers of the heart to pump blood and (2) weak electrical currents that are detectable on the body surface as the electrocardiogram (ECG). In the electrocardiogram, a dominant portion is the QRS complex, the most prominent feature of which is the R-wave that is generated when the largest mass of muscle cells depolarizes. These cells make up the ventricles, and the left ventricle is a large contributor to the ECG signal. Other features of the ECG are the P-wave (atria depolarization) and the T-wave (ventricles repolarization). (See FIG. 13A for a representative R-wave as indicated.) The QRS complex includes the Q-wave, R-wave and S-wave and is normally dominated by the R-wave. (This characterization of the QRS complex is a simplification. The example ECG of FIG. 13A does not include a recognizable S-wave. In fact, it is somewhat common that any one of the Q, R, or S-waves may be missing. And, a number of other variations in ECG polarization and depolarization sequences are possible, all well known to those skilled in the art of electrocardiology.) ECG signals vary considerably from patient to patient and among the multiple leads of an ECG measurement. The representative single-lead ECG signal of FIG. 13A is a good illustration of how, for example, the Q-wave and S-wave may not be easily recognized in an ECG signal. The R-wave also varies considerably from patient to patient but is more reliably recognized (detected) because of its dominant properties. Measurement noise from a variety of sources is also a confounding factor in ECG signals.

During certain procedures, an electrophysiologist (EP) must position and constantly reposition several different catheters for mapping and ablation in the beating heart of a patient. Typically, the EP has available a fluoroscopic imaging system that uses X-rays through the patient to make a 2D image of the heart. The EP works rapidly in to order to minimize number of fluoroscopic images to reduce as much as possible the procedure time and thus patient exposure to X-rays. Fluoroscopic images are typically obtained at rates of 7.5 or 15 images per second, and sometimes even higher, thereby usually providing many fluoroscopic images per heartbeat.

Because the contraction of the heart chambers (ventricles and atria) necessarily results in motion of the heart chamber walls and flow of blood, any catheter that is positioned in a heart chamber will move. The movement of the catheter with every heartbeat is a major complication for the EP. The motion is, however, highly repetitive since most heartbeats are very similar to immediately recent heartbeats. (This cardiac motion is the dominant confounding motion, but in addition there is a smaller, slower, and repetitive confounding motion from respiration. There may also be random motion from the patient.)

R-wave gating, the timing of imaging with respect to heartbeat, may be helpful in three ways: (1) to present a sequence of fluoroscopic images to the EP in which all of the motion of the heart and catheters during a single heartbeat is substantially removed so that from one heartbeat to the next, the EP sees essentially a stable image; (2) to select a time or range of times during which heart motion is minimal so that fluoroscopic images may be captured with the least amount of blurring during the short exposure time of a single X-ray image; and (3) to select a fluoroscopic image at a specific time of the cardiac cycle, typically diastole, which may match the same phase of cardiac cycle when, for example, a computed tomography (CT) image of the heart had been made and which is being used as the substrate for an evolving model of ablation-related information.

To present a stable image from heartbeat-to-heartbeat, a constant phase of the heartbeat is detected. The easiest and most reliable phase of the heartbeat to detect is systole, just at the instant of the R-wave. The R-wave of normal beats and ectopic (abnormal) beats occurs at the moment the ventricles depolarize and contract; thus, images of both normal and ectopic beats may be used for this purpose.

With respect to minimal cardiac motion, many images may be retained for computer analysis or presentation to the EP because during much of the normal cardiac cycle, the heart chamber walls are moving more slowly. R-wave gating identifies these time periods indirectly as timing offsets from each recognized R-wave. In selecting a particularly beneficial instant in the cardiac cycle at which to obtain a fluoroscopic image, this moment is predicted as an offset interval from the detected R-wave rather than recognizing this moment directly in the ECG. Thus, detection of R-waves in an ECG signal is an important function for such cardiac gating.

It is desirable for this R-wave gating function to be simple, reliable, accurate, and automatic, to involve a low computational burden, to be able to function on a single ECG channel, and to operate as close to real-time as possible (i.e., with minimal delay).

Figure 12:
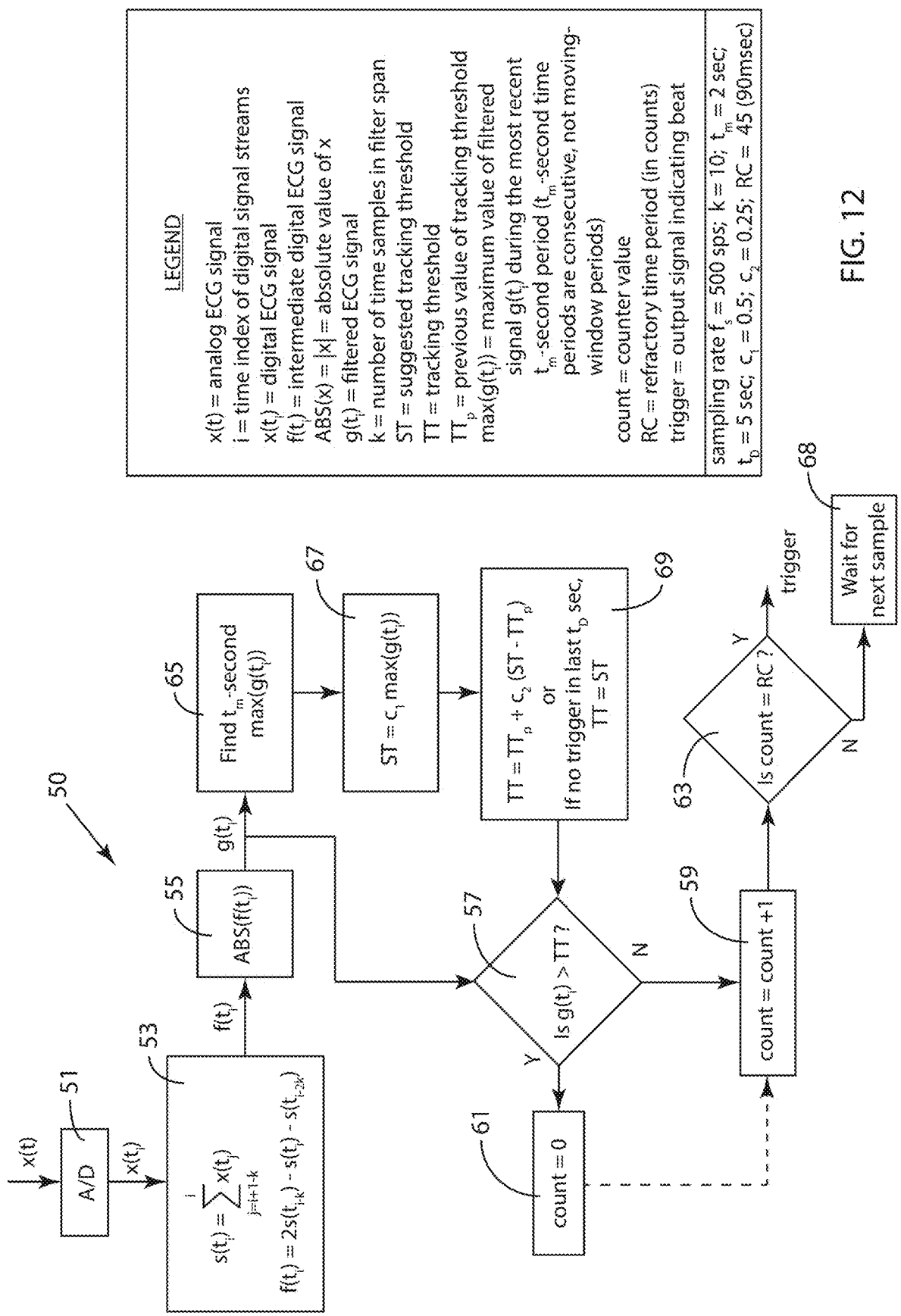
FIG. 12 is a schematic description of the inventive R-wave detector used to generate a cardiac gating signal for the image selection process of FIG. 6.

FIG. 12 illustrates an embodiment of an inventive R-wave detection system 50. FIG. 12 includes a legend which provides definitions of all of the signals and parameters shown in R-wave detection system 50. This embodiment is illustrated in generality (parameters shown as symbols) and specificity (values given for parameters at the bottom of the "Legend"). FIGS. 13A-13C illustrate three signals used within R-wave detection system 50 and described below.

As depicted in FIG. 12, a single-channel analog ECG signal x(t) from a living body being monitored is converted to a digital ECG signal $x(t_i)$ by an analog-to-digital (A/D) converter 51 (A/D sampling rate $f_s$=500 samples per second in system 50). A representative digital ECG signal $x(t_i)$ is shown in FIG. 13A. Digital ECG signal $x(t_i)$ is fed through a 25 Hz digital bandpass filter 53 to generate intermediate digital signal $f(t_i)$. A representative intermediate digital signal $f(t_i)$, generated from $x(t_i)$, is shown in FIG. 13B.

Filter 53 and all other remaining elements of R-wave detection system 50 may be realized in software programmed to compute the required quantities in a digital computer such as a PC. Filter 53 includes a boxcar filter $s(t_i)$ which is a moving-window sum of k samples of $x(t_i)$ and a second-differencing filter producing an intermediate ECG signal $f(t_i)$. In the flowchart of FIG. 12, the equations for $s(t_i)$ and $f(t_i)$ are shown. As shown in R-wave detection system 50, k has a value of 10. That is, $s(t_i)$ is the sum of the current input value $x(t_i)$ and the 9 previous values of the digitized ECG signal, and intermediate ECG signal $f(t_i)$, the bandpass filter 53 output, is a second difference of these sums $s(t_i)$.

The center frequency of a digital bandpass filter depends on the product of k and sampling period $t_s$ ($t_s=1/f_s$ seconds). In the embodiment of FIG. 12, k=10 and $t_s$=0.002 seconds. The product of these two quantities is 20 msec, corresponding to a bandpass filter center frequency of 25 Hz. These filter relationships are well known to those skilled in the art of digital signal processing.

In this embodiment, filter 53 is a symmetrical, finite-impulse-response filter which has a 60-millisecond-wide impulse response. Intermediate ECG signal $f(t_i)$ peaks approximately 30 msec (30 milliseconds) after the peak of input ECG signal $x(t_i)$, introducing approximately a 30 msec delay.

Note that $f(t_i)$ in FIG. 13B, and consequently $g(t_i)$ in FIG. 13C, are shown as having much higher signal levels than $x(t_i)$ in FIG. 13A. This is due to the fact that as shown in filter 53, the relationship for $s(t_i)$ is not divided by k (not averaged but summed over 10 values). Such embodiment is not intended to limit the structure of bandpass filter 53; it is clear that averaging or summing or using yet a different value of gain for the computation of intermediate digital signal $f(t_i)$ does not change the basic structure of the embodiment of R-wave detection system 50. Further, the signal levels shown for $x(t_i)$, $f(t_i)$, and $g(t_i)$ are arbitrary levels of digital signals, and the performance of R-wave detection system 50 is not dependent on such signal gain settings.

Intermediate ECG signal $f(t_i)$ is rectified by computing its absolute value at element 55 to produce filtered ECG signal $g(t_i)$. A representative filtered ECG signal $g(t_i)$, generated from $f(t_i)$, is shown in FIG. 13C. Filtered ECG signal $g(t_i)$ is compared to a computed ECG tracking threshold TT at a comparator element 57. If filtered ECG signal $g(t_i)$ is less than or equal to ECG tracking threshold TT, a counter 59 is incremented by one count. Counter 59 is in effect a timer since a comparison is made by comparator 57 each time a new filtered ECG signal $g(t_i)$ value is available, i.e., 500 times per second in R-wave detection system 50. In this embodiment, therefore, each count is equivalent to 2 msec. If, at comparator 57, filtered ECG signal $g(t_i)$ exceeds ECG tracking threshold TT (usually during the R-wave), counter 59 is reset to 0 as indicated by element 61 in the FIG. 12 flowchart. This reset to 0 occurs only when triggered by the comparison resulting from comparator 57 and is indicated by the dotted-line connection between counter reset 61 and counter 59.

During the period of time after a reset from counter reset 61, when filtered ECG signal $g(t_i)$ is below ECG tracking threshold TT, counter 59 is not reset and continues to count. When counter 59 reaches a predetermined refractory count RC, as determined by a comparator element 63, an R-wave trigger is outputted, and this trigger is provided to other portions of the C3DLS process or used by other systems requiring a cardiac gating signal. In this embodiment, refractory count RC has a value of 45 which corresponds to a refractory period of 90 msec (45×2 msec sampling period). With this set of parameters, when an R-wave trigger is generated, R-wave detection system 50 is indicating that an R-wave has occurred approximately 120 msec ago (approximately a 30 msec filter delay plus 90 msec refractory period). If the count from counter 59 is not equal to RC in comparator 63, the process simply waits for the next sample to occur as shown in functional element 68.

A portion of each cycle of a heartbeat is called the refractory period, a period during which the heart muscle is repolarizing. During such period, the next heartbeat cannot occur; i.e., until repolarization is complete. The purpose of refractory count RC is to prevent double triggers from being generated within a single heartbeat.

Figure 13D:
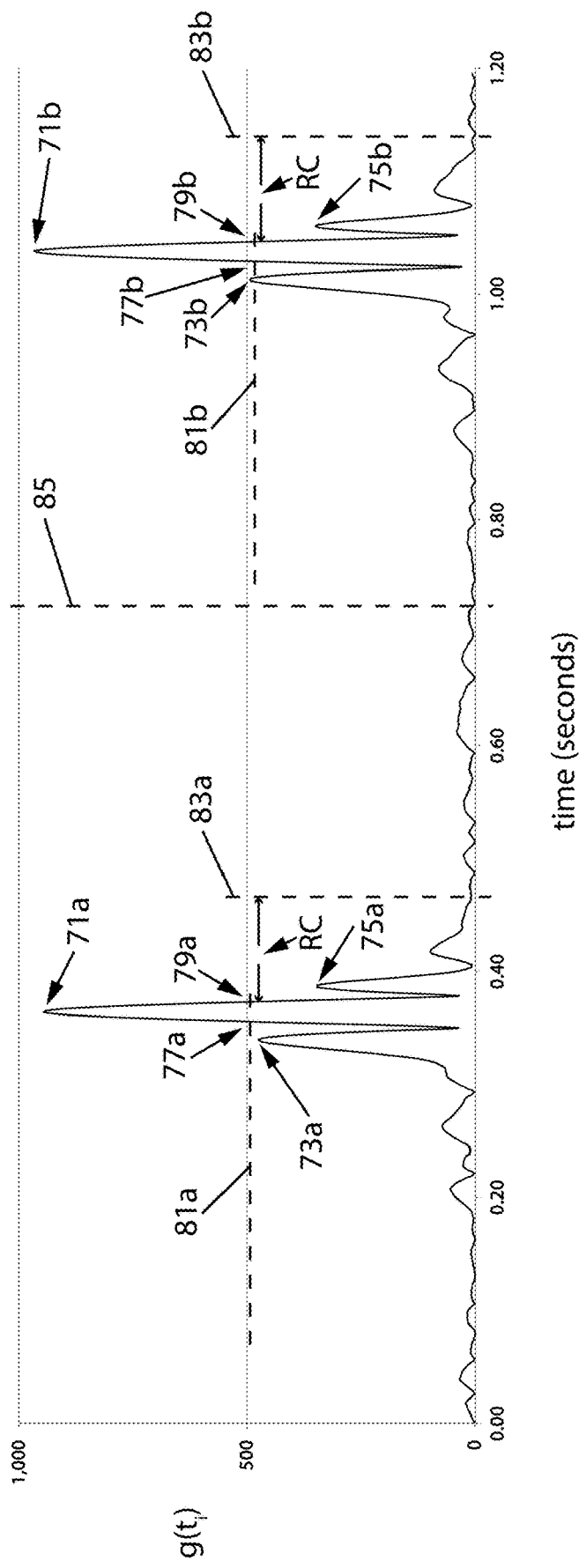
FIG. 13D is a 2-heartbeat portion of the signal $g(t_i)$ of FIG. 13C annotated to illustrate certain steps within the inventive R-wave detector of FIG. 12.

FIG. 13D is an enlarged portion of the filtered ECG signal $g(t_i)$ from FIG. 13C as indicated in FIG. 13C. FIG. 13D shows two heartbeat segments of the representative filtered ECG signal $g(t_i)$. The two heartbeats are approximately 0.67 seconds apart. The first heartbeat segment along the time axis is referred to by reference numbers ending in the letter "a", and like features of the second heartbeat segment have like reference numbers having the letter "b". Among other portions of the filtered ECG signal $g(t_i)$, each heartbeat includes signal segments around peaks 71a and 71b generated primarily by the corresponding R-waves in digital ECG signal $x(t_i)$. On the leading side of peaks 71a and 71b are smaller peaks 73a and 73b, respectively, and on the trailing side of peaks 71a and 71b are smaller peaks 75a and 75b, respectively. Within the remaining regions of signal $g(t_i)$ in FIG. 13D are signals with levels much lower than the peaks as just described.

R-wave detection system 50 includes the dynamic setting of ECG tracking threshold TT, and ECG tracking threshold TT is independent of all previous levels of the ECG signal at which R-wave triggers have occurred. Prior art R-wave detector systems which include dynamic setting of a tracking threshold typically set the tracking threshold level based on an average of previous ECG signal levels at which triggers had occurred or at a level determined by some other function of previous R-wave-triggered processed ECG signal levels. Such previous-trigger-level-dependent R-wave detectors may operate well as long as the cardiac performance does not vary too much or as long as the ECG signal does not contain too much noise. In particular, arrhythmias or other cardiac electrical abnormalities cause such prior art R-wave gates to perform poorly.

In R-wave detection system 50, filtered ECG signal $g(t_i)$ is monitored by element 65 to find its maximum value within a predetermined time period $t_m$. Time periods $t_m$ are not moving-window periods but a series of sequential periods $t_m$ seconds long. Finding the maximum value of filtered ECG signal $g(t_i)$ in such a fashion allows R-wave detection system 50 to adapt to changing signal levels within ECG signal $x(t)$. Based on the most recent maximum value of $g(t_i)$, a suggested ECG tracking threshold ST is computed in element 67 as a constant $c_1$ times the maximum value of $g(t_i)$. In this embodiment, $c_1=0.5$. Then, in element 69, ECG tracking threshold TT is computed, as follows:

$$TT=TT_p+c_2(ST-TT_p)$$

where $TT_p$ is the previously-set value of TT and $c_2$ is a constant. The computed value for ECG tracking threshold TT is used in comparator 57 unless for a predetermined dropout period $t_D$ after the last trigger was generated, a new trigger has not been generated, at which point ECG tracking threshold TT is set to ST. In this embodiment, predetermined dropout period $t_D$ is set to 5 seconds.

An initial value for tracking threshold TT may be set at an experimentally-determined numerical value. However, the dynamic setting of tracking threshold TT quickly converges to its proper value in a few time periods $t_m$.

ECG tracking threshold TT is repeatedly adjusted to adapt to a level equal to a fraction of suggested ECG tracking threshold ST. (In the embodiment of FIG. 13, that fraction is 0.5.) To gradually adjust ECG tracking threshold TT, suggested threshold ST is derived from independent $t_m$-second time periods of filtered ECG signal $g(t_i)$. (Such time periods are independent in that they are sequential with no overlap, i.e., these time periods are not moving-window periods.) Filtered ECG signal $g(t_i)$ is inspected for $t_m$ seconds to find its maximum within that $t_m$-second period. Thus, in this embodiment for that 2-second period, a good choice of ECG tracking threshold TT is one-half of the maximum value of $g(t_i)$ during that period. However, the next two seconds of filtered ECG signal are inspected similarly and independently, and ECG tracking threshold TT is gradually adjusted at the end of every two seconds (in general, $t_m$ seconds) so that TT tends to track (adapt to) the independent suggested thresholds ST.

The adaptation process of element 69 operates to adjust ECG tracking threshold TT by a fraction $c_2$ of the difference between its immediately previous value $TT_p$ and each new suggested threshold ST. This process smooths the response of ECG tracking threshold TT to changes in suggested threshold ST (changes in the maximum value of filtered ECG signal $g(t_i)$ in sequential fixed $t_m$-second periods). The amount of smoothing of ECG tracking threshold TT depends on the value of the $c_2$, and a greater amount of smoothing also adds more time lag in the response of ECG tracking threshold TT to changes in suggested threshold ST. Values of $c_2$ closer to 0 provide a greater amount of smoothing and more lag in the response. Values of $c_2$ closer to 1 produce less smoothing and quicker response.

ECG tracking threshold TT is also adjusted if no R-wave trigger has occurred for a period of $t_D$ seconds. This occurs in the rare case when, because of more rapid changes in filtered ECG signal $g(t_i)$, ECG tracking threshold TT has not responded quickly enough and the R-waves are not being detected. In the embodiment of FIG. 12, $t_D$ is 5 seconds. When this occurs, ECG tracking threshold TT is set to the current value of suggested threshold ST, causing heartbeats to start being detected immediately.

As described above, the embodiment of the inventive R-wave detection system 50 of FIG. 12 is shown with parameter settings as follows: digital sampling rate=500 sps; k=10; $t_m=2$ seconds; $c_1=0.5$; $c_2=0.25$; $t_D=5$ seconds; and RC=45. It has been determined that such specific set of parameters operates well in R-wave detection system 50, but such parameter values are not intended to limit the scope of the invention.

A sampling rate of 500 sps and a boxcar window sum of 10 samples sets filter 53 as a 25 Hz bandpass filter. By incorporating a bandpass filter with a higher center frequency (~25 Hz) than is typical (~15 Hz), inventive R-wave detection system 50 is able to more strongly reject T-waves and P-waves while allowing sufficient R-wave signal content to be available for detection purposes. Within the scope of this invention, bandpass filter 53 may have a center frequency other than 25 Hz. If the center frequency of bandpass filter 53 is set too high, however, ectopic or bundle branch R-waves may be undesirably rejected.

Predetermined time period $t_m$, over which maximum values of $g(t_i)$ are determined in element 65, needs to be long enough to be sure to contain at least one R-wave for the full range of expected heart rates. Thus, a minimum of about 1.5 seconds is desirable. A value of $t_m$ of 2 seconds corresponds to ensuring that a heart rate of 30 bpm will be properly processed. Longer periods of time cause the adaptation of ECG tracking threshold TT to changes in the ECG signal to be undesirably delayed.

The setting of ECG tracking threshold TT at about one-half ($c_1$=0.5) of filtered ECG signal $g(t_i)$ maxima is appropriate since lower settings risk generating triggers on P-waves and T-waves and much higher levels risk missing R-waves that are of lower amplitude during part of the respiration cycle or from lower-amplitude ectopic heartbeats. A good range for values of $c_1$ is within about 0.4 to 0.7.

The constant $c_2$ affects the rate at which adaptation to ECG signal changes occurs. It has been found that $c_2$=0.25 provides excellent adaptation rates; smaller correction steps slow adaptation and larger correction steps overreact to isolated artifacts in the ECG signal. Values of $c_2$ within a wide range of about 0.15 to 0.8 allow the adaptation rate to be selected as desired.

The length of time for the refractory period is set by setting the refractory period parameter RC which, as explained above, is a count value. The refractory period (time) is RC times the sampling period of the digital signals. In the embodiment of FIG. 12, the refractory time period is 45×2 msec=90 msec. Refractory time periods within the range of 30 to 250 msec provide a useful range of values with the corresponding count values for the parameter RC. A shorter refractory period risks generating double triggers within a single QRS complex; longer refractory periods introduce additional delay. Also, longer refractory periods can result in missed beat detections when ectopic beats are very early or very high heart rates are present. Depending on a specific ECG signal, setting RC to yield triggers in the most desirable region of the heartbeat can be achieved.

Referring now to FIG. 13D, two heartbeats are shown. These heartbeats include a series of peaks as defined above. In describing the operation of R-wave detection system 50, it is assumed that from a previous 2 sec time period $t_m$, ECG tracking threshold TT (81a) was determined to have a value of 490 (shown but not quite to scale). As system 50 proceeds in time to process sequential values of filtered ECG signal $g(t_i)$, none of the values of $g(t_i)$ associated with peak 73a are above ECG tracking threshold TT (81a). At the point along $g(t_i)$ indicated by reference number 77a and all of the sampled points between 77a and 79a, $g(t_i)$ is above ECG tracking threshold TT (81a). Thus, at each sampled point in this region (77a-79a), counter reset 61 resets counter 59 to 0. At each sample point of $g(t_i)$ past the point 79a, counter 59 is incremented by 1, and when counter 59 has a value equal to RC (45 counts), R-wave detection system 50 outputs a gating trigger at the time indicated by reference number 83a. There are several ways for the trigger output to be conditioned, such as producing a fixed-length pulse; these ways are all well known to those skilled in the art of signal processing, and the operation of R-wave detection system 50 is not dependent on such conditioning.

As the process proceeds, element 65 monitors the values of $g(t_i)$ to find the maximum value of $g(t_i)$ during the 2-sec time period $t_m$ ending at the time corresponding to dotted line 85. That maximum occurs at peak 71a, and in this example has a value of 945. As time progresses past line 85, a new value of ECG tracking threshold TT (now 81b) is established by the calculation in element 69, as follows: TT (81b)=490+0.25*(945/2−490)=485.63. (The time axes of FIGS. 13A-13D are scaled to start at t=0; however, this time representation is completely arbitrary.)

In comparing the operation of R-wave detection system 50 around peak 71b, note that peak 73b is above ECG tracking threshold TT (81b) and so for any sampled points of $g(t_i)$ within peak 73b which are above TT (81b), counter reset 61 will reset counter 59 to 0. However, the point 77b along $g(t_i)$ (and all of the points between 77b and 79b) also cause counter 59 to be reset to 0 prior to counter 59 reaching the value RC (45 counts). Thus, point 79b is the final point along $g(t_i)$ to restart the count in counter 59, and an R-wave trigger is then generated at the time indicated by reference number 83b.

One advantage of the inventive R-wave detection system is that it produces a very low rate of false positive detections, i.e., the rate at which a trigger occurs when no R-wave has occurred is extremely low. Because of this, using multiple R-wave detection systems in parallel can improve the overall performance of R-wave detection. For example, when an ectopic or short R-wave is missed in one ECG channel, it is very often detectable in a different ECG channel. One aspect of the present invention is to combine multiple R-wave detection systems into a composite R-wave detection system for increased accuracy.

Figure 14A:
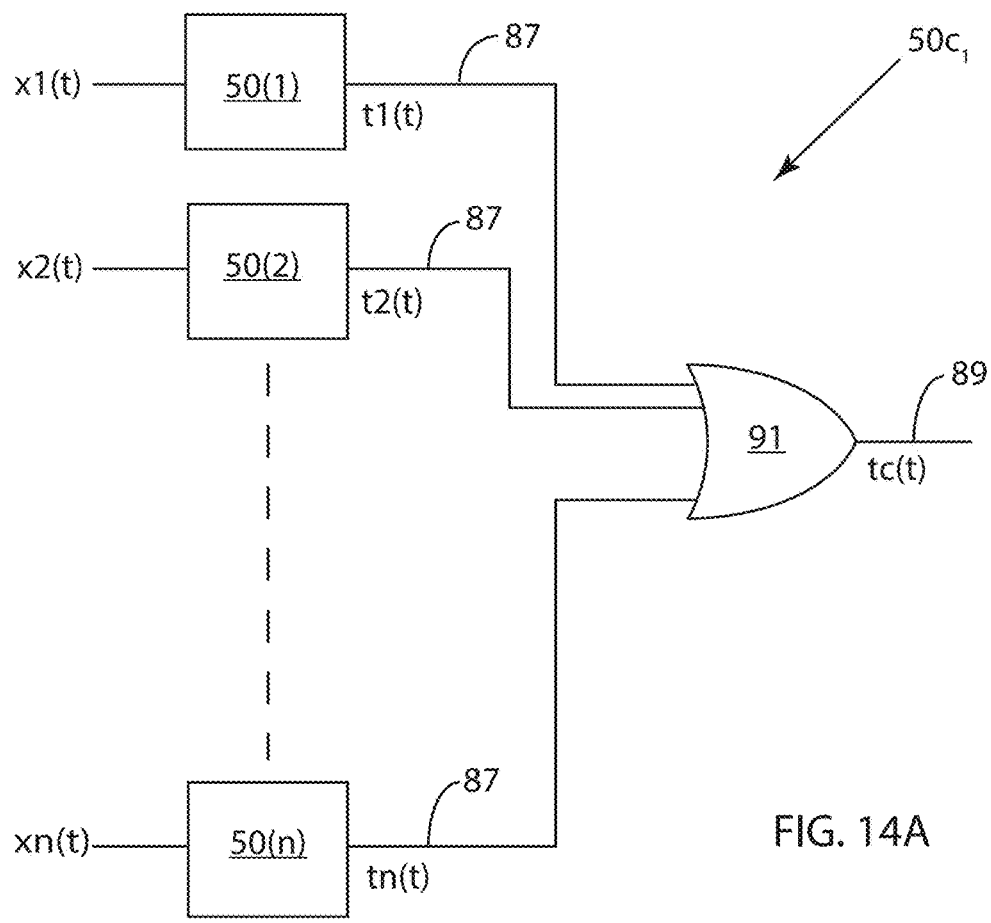
FIG. 14A is a schematic description of an embodiment of a composite R-wave detector using multiple channel R-wave detectors as inputs to an OR-gate.
Figure 15A:
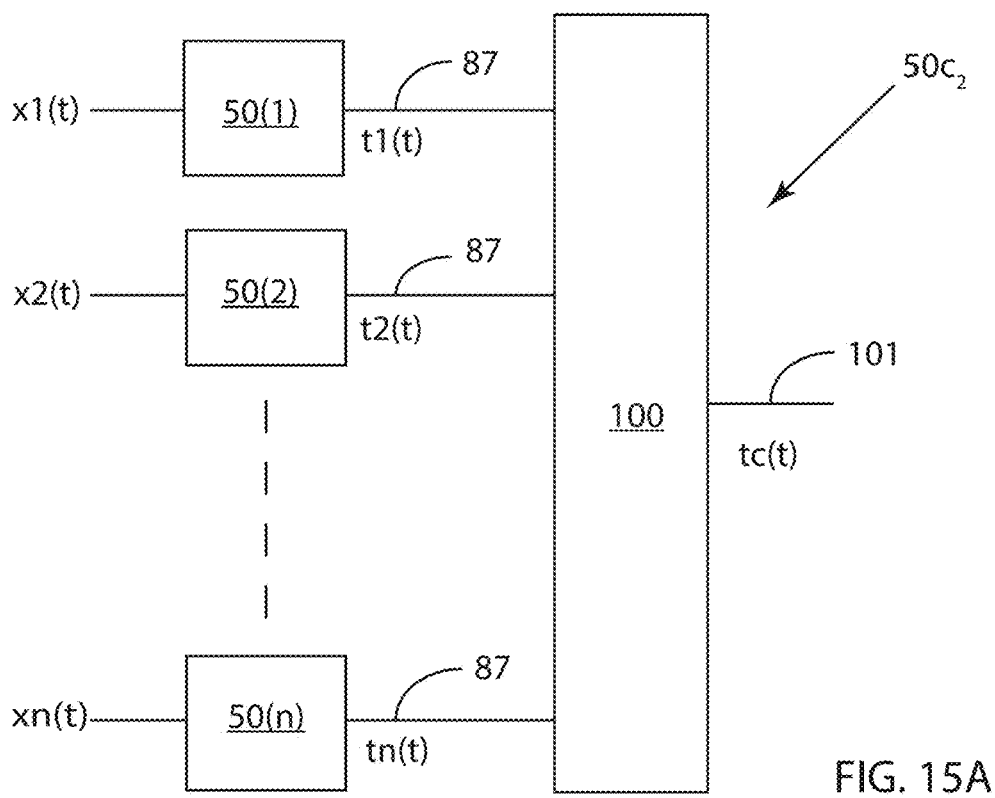
FIG. 15A is a schematic description of an alternative embodiment of a composite R-wave detector using multiple channel R-wave detectors as inputs.

ECG signals are typically available as multiple-channels from electrodes placed on different locations on a living body. The individual channel signals are similar in character but also somewhat different both in detailed shape and phase. FIGS. 14A and 15A illustrate two embodiments of such a composite R-wave detection system.

Referring first to FIG. 14A which illustrates one embodiment, composite R-wave detection system $50c_1$. Composite R-wave detection system $50c_1$ includes n channel ECG signals as inputs into n channel R-wave detection systems 50(1)-50(n). Such channel R-wave detection systems are identical in structure to R-wave detection system 50, but each operate independently on its own corresponding channel ECG signal to generate its own channel R-wave trigger signal (herein sometimes referred to as a channel trigger signal). This set of channel trigger signals is indicated by reference number 87 and by t1(t), t2(t), . . . tn(t), respectively. Composite R-wave detection system $50c_1$ includes an OR-gate 91, the output tc(t) of which is the composite R-wave trigger signal 89 which indicates the detection of R-waves in the multi-channel ECG signal.

Figure 14B:
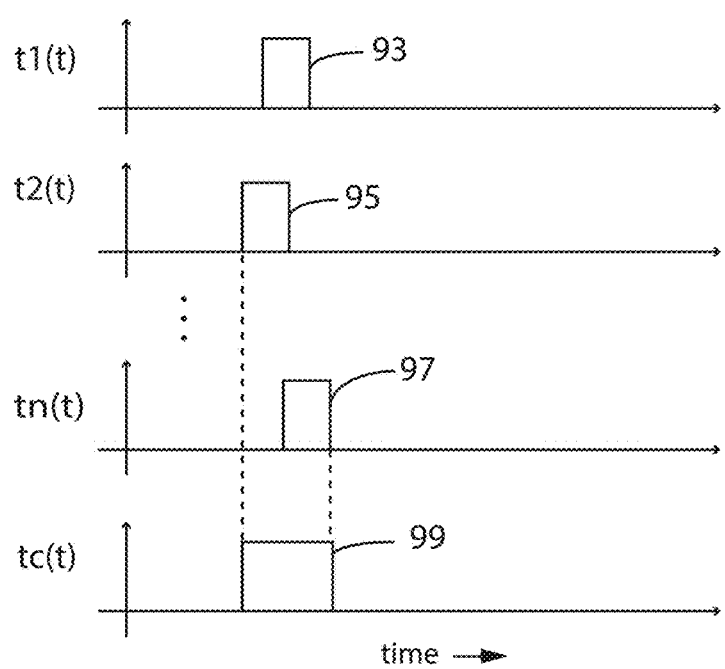
FIG. 14B is a timeline illustration of the operation of the composite R-wave detector of FIG. 14A.

FIG. 14B further illustrates the operation of composite R-wave detection system $50c_1$. Four timeline functions are shown, three channel trigger signals 87 and composite R-wave trigger signal 89. Each of these signals is represented as either being HIGH or LOW (zero) in normal logic representation. Such representation is not intended to be limiting in any way. Channel R-wave detection systems 50(1)-50(n) include signal conditioning of channel trigger signals t1(t)-tn(t) such that each time a channel R-wave detection system (50(1) through 50(n)) detects an R-wave, a pulse of fixed duration is generated in the corresponding channel R-wave trigger signal.

Pulses 93, 95, and 97 are such fixed-duration pulses in individual channel trigger signals. (Such signal conditioning is well known by those skilled in the art of signal processing and is not shown herein.) Composite R-wave trigger signal 89 is the output of OR-gate 91. Output tc(t) is HIGH when any of the individual channel R-wave trigger signals is HIGH, as shown in FIG. 14B. The leading edge of the resultant output pulse 99 of tc(t) may be regarded as the time that the composite R-wave trigger occurred but other times related to pulse 99 may also be regarded as such.

The time width of pulses 93-97 may be set to a period of time which when added to the time period corresponding to refractory count RC for the individual RC values of the channel R-wave detectors of composite R-wave detector $50c_1$, sums to the period of time corresponding to refractory count RC for an R-wave detector 50 operating alone. Thus, if the time period corresponding to refractory period RC for the channel R-wave detectors is set to about 50 msec, then the length of pulses 93-97 may be about 40 msec. A range of suitable values for such sum may be from 50 to 200 msec.

FIG. 15A illustrates a second embodiment of a composite R-wave detector, composite R-wave detection system $50c_2$. Composite R-wave detection system $50c_2$ includes similar inputs as composite R-wave detection system $50c_1$ and the same channel R-wave detection systems to generate channel trigger signal t1(t)-tn(t). Channel R-wave trigger signals t1(t)-tn(t) are inputs to a trigger-window filter 100. Trigger-window filter 100 outputs a composite R-wave trigger in a trigger output tc(t) (101). Trigger-window filter 100 is configured to output a trigger in trigger output tc(t) when it receives a channel R-wave trigger from any one of the channel R-wave detectors. When such a trigger occurs in tc(t), all channel trigger signals from the channel R-wave detectors not triggering composite R-wave detector $50c_2$ are ignored for a predetermined time period (lockout period $t_{LO}$) after composite R-wave detector trigger output tc(t) is triggered.

Figure 15B:
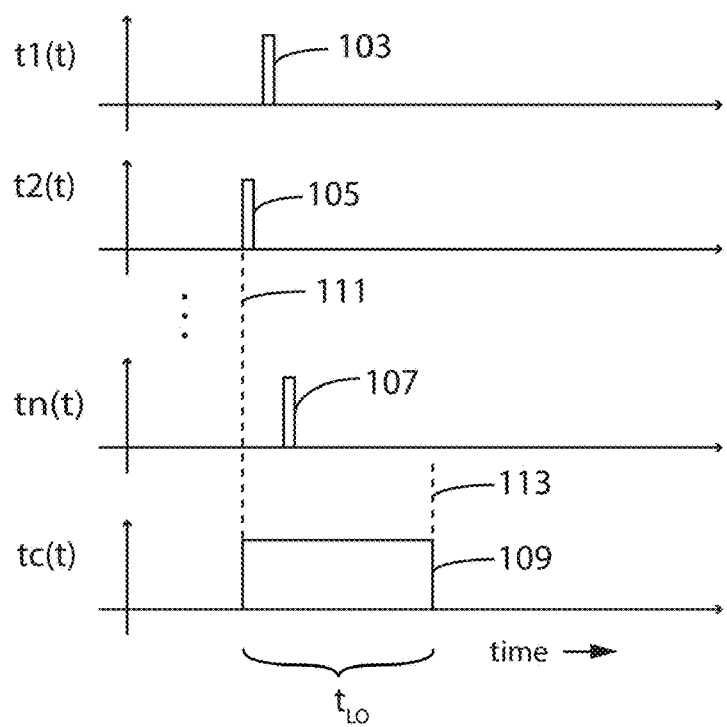
FIG. 15B is a timeline illustration of the operation of the composite R-wave detector of FIG. 15A.

FIG. 15B illustrates one such triggering. Channel R-wave trigger signals t1(t)-tn(t) each contain a channel R-wave trigger represented by pulses 103, 105 and 107. Pulse 105 is the first to be received by trigger-window filter 100, and this time is indicated by dotted line 111 (hereinafter called time 111). Prior to time 111, trigger-window filter 100 was ready to receive channels triggers on all of its inputs 87. After time 111, trigger-window filter 100 is configured to ignore all other channel triggers received for a predetermined period of time (lockout period $t_{LO}$), in this embodiment shown as the difference between time 113 and time 111. Composite R-wave trigger output tc(t) is shown as a constant pulse 109 of duration $t_{LO}$, but this specific pulse shape is not intended to be limiting; any suitable pulse shape may be used.

Trigger-window filter 100 may be configured to trigger on other than the first-to-be-received channel R-wave trigger signal. For example, trigger-window filter 100 may be set to trigger on the second or third or other received channel R-wave trigger signal.

The time width of lockout period $t_{LO}$ is set to ensure that all of the channel R-wave triggers for a single heartbeat have occurred prior to the end of lockout period $t_{LO}$. The range of suitable values for $t_{LO}$ may be about from 150 to 300 msec, and $t_{LO}$ may preferably be set to about 200 msec.

In composite R-wave detections systems $50c_1$ and $50c_2$, each of the channel R-wave detection systems 50(1)-50(n) may be set to utilize the same parameter values or may be set to utilize parameter values which vary among the channel R-wave detection systems.

It should be noted that the inventive composite R-wave detection system need not utilize multiple inventive R-wave detection systems of the type embodied as R-wave detection system 50 as channel R-wave detection systems. Other R-wave detectors may be utilized to process the channel ECG signals and generate channel R-wave trigger signals. However, the fact that channel R-wave detections systems 50 output extremely few false positive triggers is what enables the inventive composite R-wave detection system to be beneficial.

Referring again to FIG. 6, image selection 23 may also include respiration gating provided by respiration sensor 45 and respiratory gate 47. Respiration results in a cyclic motion of the organs in the thorax and, to some extent, the abdomen. In a manner similar to cardiac gating described above, by tracking the motion of the catheter and creating a motion profile, the phases of the respiratory cycle during which motion is minimal are identified, for example, end inspiration and end expiration. Images during these minimal-motion phases are selected to minimize the effect of respiratory motion on the estimates of catheter-tip location.

Respiration sensor 45 as used herein includes any type of signal source which derives information regarding respiration from a living body. These include but are not limited to direct-measurement devices, images (X-ray, optical, etc.) of objects and structures which are moving in phase with respiration, and ECG signals which contain some respiration-correlated information. Any of these respiration sensors 45 may be used to generate a signal indicative of respiration movement and as an input to respiratory gate 47.

Respiration sensors 45 which directly measure body movement caused by respiration are well known by those skilled in the art of medical instrumentation. For example, transducers mounted in belt-like structures are used to measure abdominal or thoracic motion from which a useful sensor signal is derived. Respiratory gate 47 simply triggers image selector 38 at points during periods of little or no movement (or at some other desired point) in order to select the preferred images.

Alternatively, an estimate of catheter-tip motion may be made by evaluating the position of the catheter tip in a series of fluoroscopic images. This is done by comparing the (x, y) position of the catheter tip from image-to-image, and computing the distance moved in the plane of the detector from image-to-image. Minimum motion is indicated by sequential images in which the movement between images is the smallest.

Further, some channels of ECG signals may contain variations which correlate with respiration. By applying filtering and other signal processing techniques well known to those skilled in the art of signal processing, it is possible extract such respiration-correlated information and use it as an input to respiratory gate 47.

Figure 8:
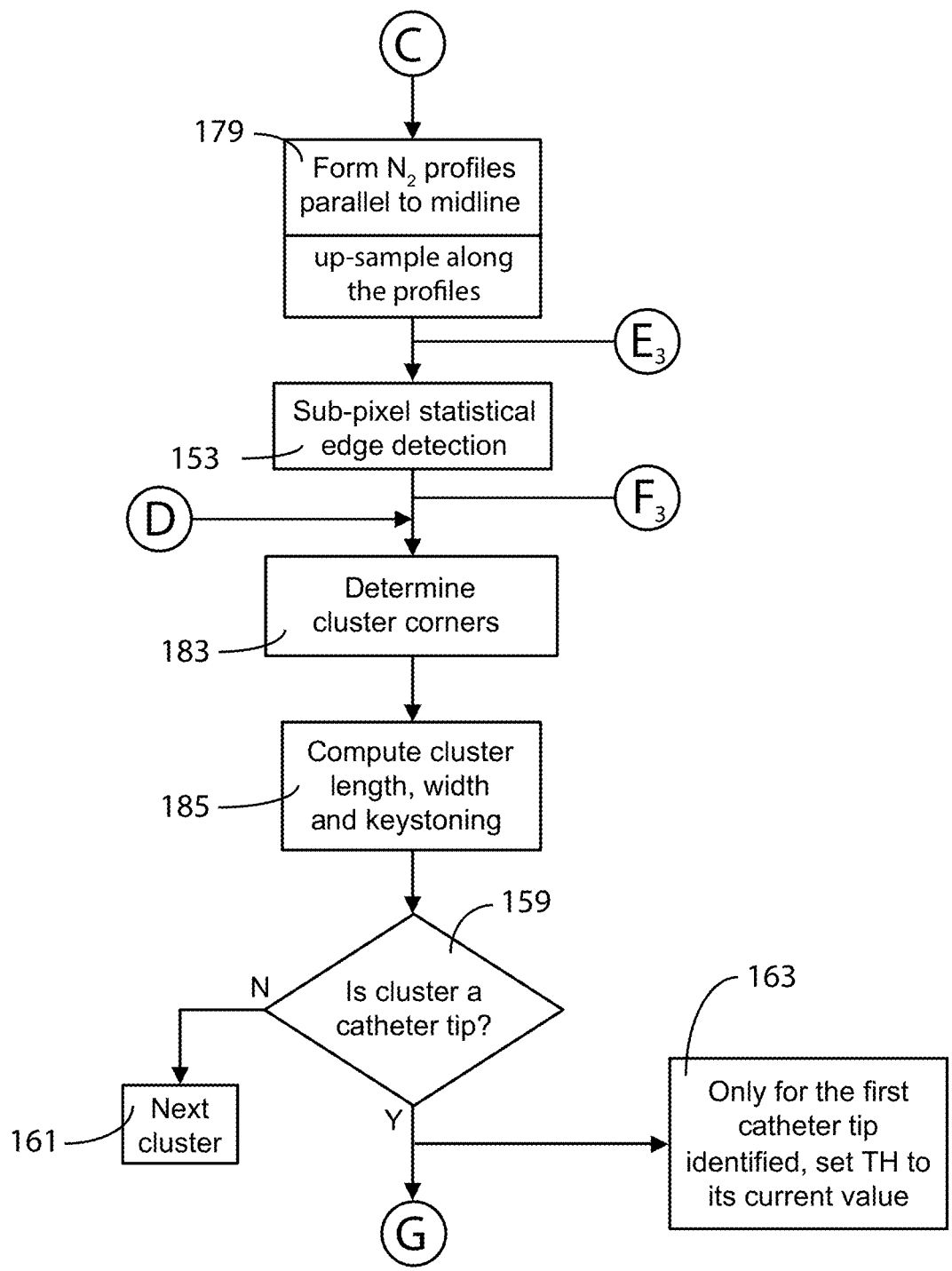

Referring again to FIG. 4, when an image has been selected to be processed within C3DLS 20, the inventive method embodied in C3DLS 20 proceeds to the steps of (1) forming clusters (functional block 25) as candidate images of a medical object (e.g., catheter tip), (2) identifying a catheter-tip image from among candidate clusters (functional block 27), and (3) determining the sub-pixel catheter-tip image dimensions (functional block 29). These steps are described in the sections that follow and are illustrated in FIGS. 7, 8 and 9.

The circled letters B and G represent the starting and ending points of this subset of steps in the method embodied in C3DLS 20. At the starting point (B) at the top of FIG. 7, the data of the selected image is in its raw form, that is, it has not been changed from the data stream that is provided by video acquisition 37. At the ending point (G) of this subset of steps at the bottom of FIG. 8, a catheter-tip image has been measured very accurately, providing the 2D coordinates of the corners of the catheter-tip image (cluster 203) (functional block 183) and catheter-tip image length, width, and keystoning (functional block 185). FIG. 8 illustrates method steps which branch as indicated from the schematic of FIG. 7 to carry out certain steps in parallel to a portion of the steps of FIG. 7, at which point (D), the results of the steps of FIG. 7 are combined with the results of steps 179, 153 and 181 and the process continues in FIG. 8 with steps 183 and proceeds to the point on the method indicated by the letter G. The method then continues at point G in the schematic of FIG. 4 with steps 31-35.

Figure 9:
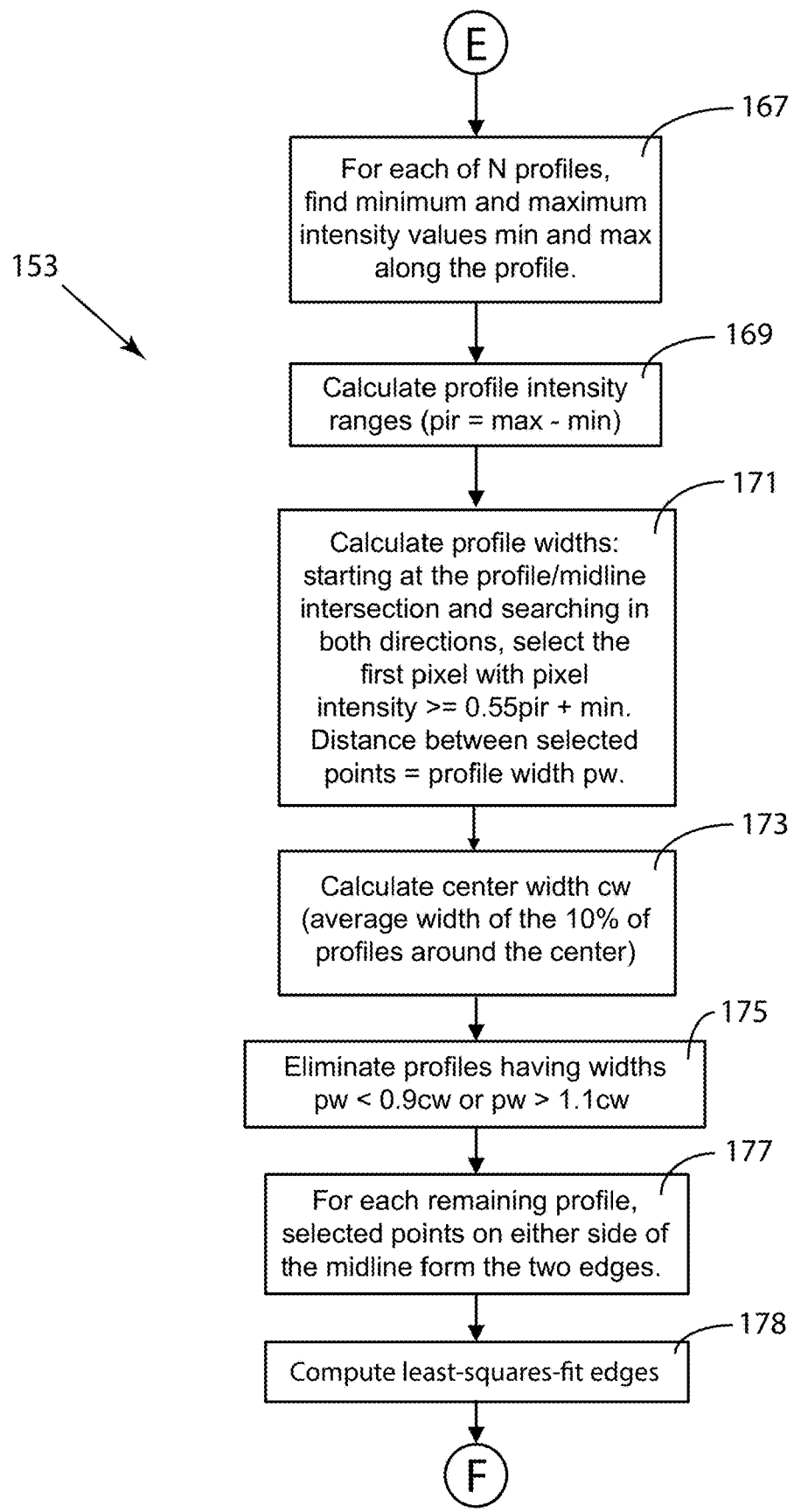

FIG. 9 illustrates in detail the method steps of the process of sub-pixel statistical edge detection (functional block 153). In C3DLS 20, such sub-pixel statistical edge detection occurs three times in sub-pixel catheter-tip image dimension determination 29. The input to sub-pixel statistical edge detection 153 is labeled with the letter E and the output with letter F. The three instances are indicated as occurring between $E_1$ and $F_1$, $E_2$ and $F_2$, and $E_3$ and $F_3$ within FIGS. 7 and 8.

Each of these steps will be described in detail in the sections which follow, particularly with reference to FIGS. 7-9.

Referring again to FIG. 7, a histogram sorting of every pixel in the selected image is performed in functional block 131, determining the distribution of pixel intensities across the entire image. For example, for a typical 8-bit X-ray image, there are one million (1,000×1,000) pixels having intensity values between 0 and 255, the darkest possible value being 0. A threshold filter is applied to the image, assigning a pixel value of 0 to each pixel having an intensity less than a threshold intensity TH and a bright pixel intensity of 255 to all other pixels.

Threshold TH of threshold filter 133 is determined iteratively based on how well clusters are delineated in a cluster formation process 135 and a cluster evaluation step 137. An initial value of threshold TH is set to assign a 0 value to 0.5% of the pixels in the image. Clusters are formed (135) and evaluated (step 137) and if it is determined that more pixels are required to form candidate clusters, threshold TH is incrementally increased in functional block 139 and steps 135 and 137 are repeated until a proper cluster satisfies the evaluation of step 137.

FIGS. 16A and 16B illustrate an example 2D X-ray image (FIG. 16A) to which a threshold filter has been applied, shown in FIG. 16B. Threshold filtering is effective in the process of automatically identifying catheter-tip images since the image of a catheter tip is generally the darkest object in such an image. (In FIGS. 16A and 16B, a catheter-tip image is labeled with reference number 201.) Thus, since the darkest pixels are singled out through threshold filtering, catheter-tip images are very likely to be found as candidate clusters in such a process.

Clusters are formed (step 135 in FIG. 7) in the following manner. A variable (Gap) is defined as the distance in pixels between dark pixels. A cluster with a Gap value of 0 means that every pixel in the cluster is a direct neighbor of another pixel in the cluster. A cluster with a Gap value of 1 means that every pixel in the cluster is a direct neighbor of another pixel in the cluster or has a 1-pixel space between it and a neighboring pixel in the cluster. Depending on the level of noise in an image, values of 0 or 1 for Gap have been found to provide good cluster formation performance.

As clusters are formed in functional block 135, a record is kept of the number of pixels in a cluster and the leftmost, rightmost, topmost and bottommost pixels in the cluster. The cluster coordinates within the image are also known. This cluster information is used to evaluate a candidate cluster against the criteria established during initialization in functional block 41A and 41B (FIG. 6). The test criteria in cluster evaluation are: (1) Is the cluster area within set catheter-tip image limits? (2) Is the cluster near enough to a last-known catheter-tip image location (if known)?

When a cluster passes such criteria tests in cluster evaluation 137 (FIG. 7), further analysis is carried out to compute the cluster center (functional block 141), compute the cluster midline (functional block 143), and determine the bounding box of the cluster (functional block 145).

One approach to finding the center of the candidate cluster is illustrated in FIG. 17. FIG. 17 includes an example candidate cluster 203 within a portion of a thresholded image. The center of candidate cluster 203 is calculated (functional block 141) as the average vector of the set of vectors to each individual thresholded pixel in cluster 203. In FIG. 17, these vectors are shown as the set of dotted lines with arrowheads. Only a few such vectors are shown in FIG. 17, but in the center computation (141), a vector representing each pixel in cluster 203 is included.

If there are n thresholded pixels (pixels which are dark) in the image, then the x-component of the average vector (center) is simply $X_{av}=1/n*\Sigma x_i$ and the y-component is $Y_{av}=1/n*\Sigma y_i$ where the summations are carried out over all n pixels. In FIG. 17, the resulting center vector $(X_{av}, Y_{av})$ is shown as vector 205.

Figure 18:
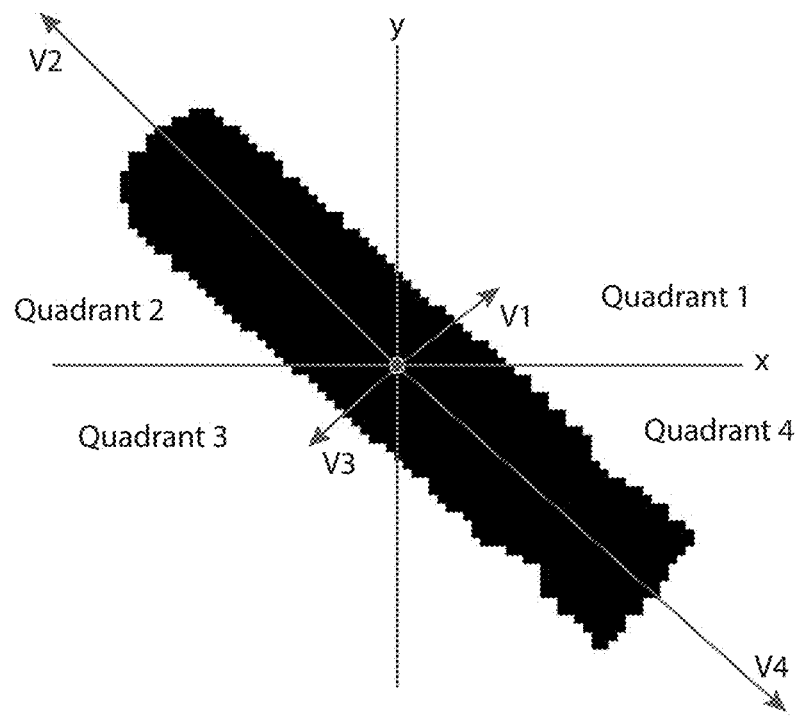
FIG. 18 illustrates one embodiment of a method to compute the longitudinal midline of a cluster of pixels in a thresholded image.

After computing the center of candidate cluster 203, a computation of a longitudinal midline of cluster 203 is performed in functional block 143. A vector representing the longitudinal axis is generally parallel to the long axis of cluster 203 and bisects cluster 203. Vectors for each thresholded pixel (from the center) are used for this calculation. As shown in FIG. 18, quadrant vectors V1, V2, V3 and V4 represent the sum of each vector in the four quadrants of the thresholded image, respectively. (Note that these vectors are not scaled precisely in FIGS. 18, 19A and 19B.)

Figure 19A:
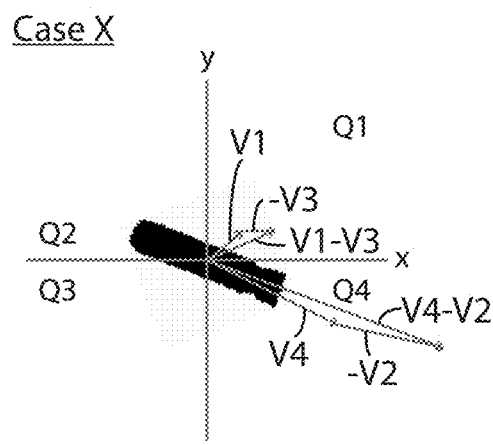
FIGS. 19A and 19B illustrate two cases of the method of FIG. 18.
Figure 19B:
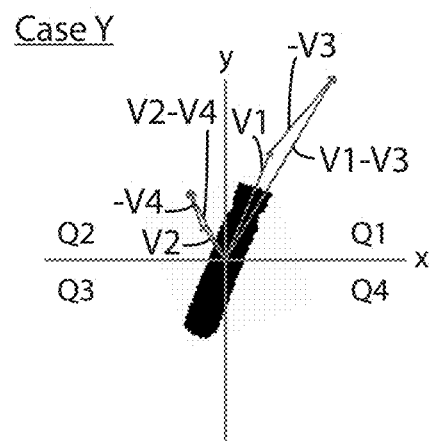

The longitudinal axis vector $V_{midline}$ is a composite of quadrant vectors V1, V2, V3 and V4 from the four quadrants. The composition of $V_{midline}$ depends on whether the main axis is predominantly along the X axis or Y axis as illustrated in FIGS. 19A and 19B. The main (dominant) axis, X or Y, is defined as the axis which contains the longest projection of any of the four quadrant vectors V1, V2, V3, V4. For example, in Case X of FIG. 19A, the longest projection of V1 is along the x-axis while in Case Y of FIG. 19B, the longest projection of V1 is along the y-axis.

The vectors from diagonal quadrants (Q1 and Q3; Q2 and Q4) are added to calculate their total contribution along either the positive x-axis (Q1 and Q4) or along the positive y-axis (Q1 and Q2). From FIG. 19A, in the x-axis case, the longitudinal axis vector is $V_{midline}=(V1-V3)+(V4-V2)$ $=V1-V2-V3+4$. Similarly for the y-axis case of FIG. 19B, the vectors along the positive Y axis are V1-V3 and V2-V4, and the longitudinal axis vector is $V_{midline}=(V1-V3)+(V2-V4)=V1+V2-V3+V4$.

Figure 20:
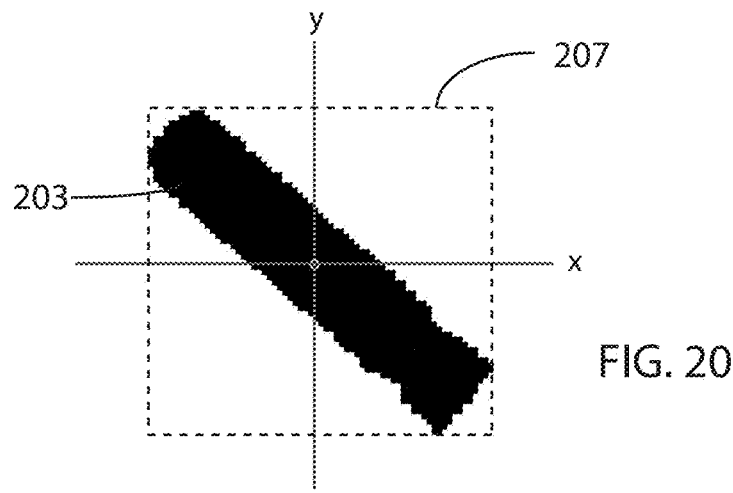
FIG. 20 illustrates a bounding box containing a cluster image.

Referring again to FIG. 7, in functional block 145, a bounding box which bounds candidate cluster 203 is found by simply determining the rectangle formed from the leftmost, rightmost, topmost and bottommost pixels of cluster 203. These values are known from cluster formation process 135. FIG. 20 illustrates such a bounding box 207 (dotted lines) of cluster 203.

Referring again to FIG. 4, after a cluster has been identified as a candidate catheter-tip image and its image center, midline and bounding box have been found (functional blocks 141-145), the processing of such cluster image within C3DLS 20 includes operations on the original pixel intensity data in the image and no longer on the thresholded image pixels. The sub-pixel catheter-tip image measurement operations (functional block 29) described herein are referred to as pixel-level geometric calculations and are an important feature of the present inventive method for automatically determining the 3D position and orientation of a catheter tip in a living body using single-plane plane fluoroscopy. More detail describing the steps of sub-pixel catheter-tip image measurement 29 within C3DLS 20 is illustrated in FIGS. 7-9.

A primary characteristic of pixel-level geometric calculations is that such calculations permit statistics to be applied during analysis since the pixel intensities are not transformed by filters. In the inventive C3DLS method, in the steps of determining sub-pixel catheter-tip image dimensions, statistics are used to achieve the desired sub-pixel accuracy at very high speeds. Many image-processing techniques include the use of filters which perform complex operations on the pixel intensities but which also transform the intensity data into forms which do not preserve the original data values, thus preventing statistical operations on the original data values.

Another characteristic of pixel-level geometric calculations as described herein is that these calculations can be completed very rapidly. An important object of the present invention is to provide a system which can compute 3D information from 2D X-ray images in real time or near real time such that C3DLS can be used contemporaneously with an interventional medical procedure such as cardiac ablation. Although C3DLS 20 is computationally intensive, pixel-level geometric calculations as described in the various steps in the inventive method have a speed advantage over many other image-processing techniques and contribute to achieving such high-speed performance.

Referring again to FIG. 7, the area of bounding box 207 determined in functional block 145 is expanded to include image area around bounding box 207 to ensure that enough background area around the catheter-tip image is available in subsequent calculations to capture information about background noise away from the cluster image. In embodiment C3DLS 20, bounding box 207 is expanded by 3× in both the X and Y coordinates, although the value (3) of the expansion factor is not intended to be limiting for bounding box expansion in functional block 145.

Figure 21:
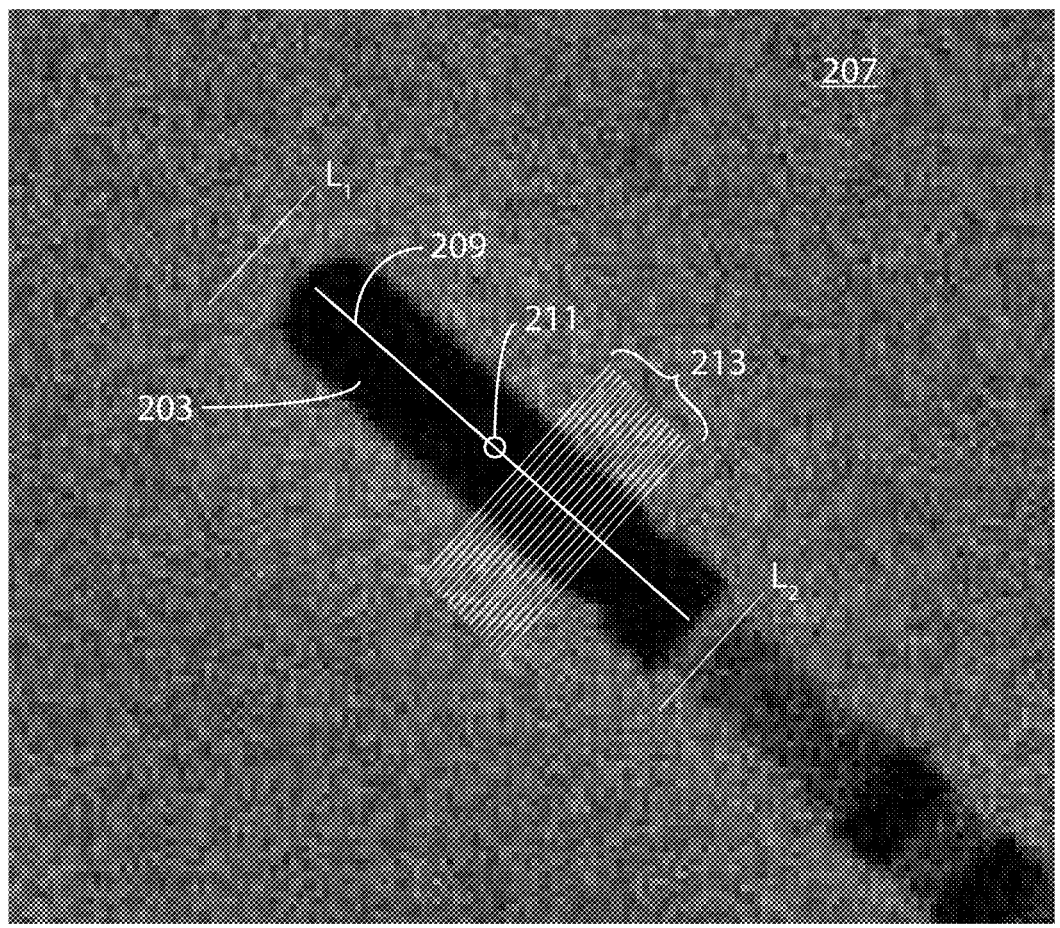
FIG. 21 is an image of a cluster which is a candidate to be identified and measured as a catheter tip. Profiles used to carry out measurement within the inventive method are shown.

The next step, illustrated as functional block 151, is to form a number of image profiles perpendicular to the longitudinal image midline computed in step 143 and to up-sample the image along such profiles. FIG. 21 illustrates candidate cluster 203 in a portion of bounding box 207. Also illustrated in FIG. 21 are a longitudinal midline 209 passing through a cluster center 211 computed in step 141 and several example profiles 213. The profiles represent image intensities along lines perpendicular to midline 209. Functional block 151 indicates $N_1$ such profiles being formed. Note that FIG. 21 does not show all $N_1$ profiles; only 16 profiles are shown. The number of profiles $N_1$ is such that at least one profile passes through each pixel of cluster 203 and outside of cluster 203 in both directions along each profile 213 so that all possible intensity variations in the image are represented in $N_1$ profiles 213. It is particularly desirable that $N_1$ be such that two (2) profiles intersect each such pixel.

Note that the distance between profiles 213 shown in FIG. 21 is also not representative of how close profiles 213 should be to one another. $N_1$ profiles 213 are more tightly packed than the 16 profiles 213 shown, and profiles 213 may be distributed along the entire length of cluster 203 and past each end. Thus, profiles 213 may extend between lines $L_1$ and $L_2$ shown in FIG. 21. Note that the range over which profiles may be distributed across a cluster depends on the physical shape of the medical object being imaged and the choice of geometry being tracked with C3DLS. The range indicated in FIG. 21 is therefore not intended to be limiting.

Figures 22, 23:
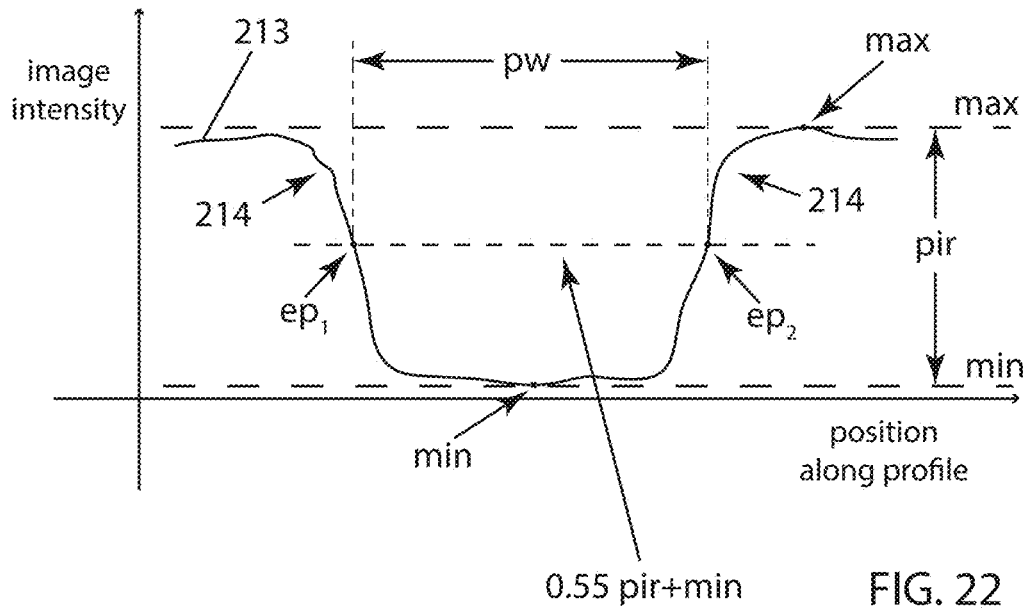
FIG. 22 illustrates one profile from the example profiles shown in FIG. 21.
FIG. 23 is an illustration of the calculations of one method to up-sample a digital image.

FIG. 22 illustrates one profile 213. The abscissa of the graph of FIG. 22 is position along a line perpendicular to midline 209, and the ordinate is the image intensity of the points along such line. Points in candidate cluster 203 are dark compared to the image background such that each profile 213 has a shape generally as illustrated in FIG. 22.

Referring again to FIG. 7, functional block 151 also includes the step of up-sampling the image along each profile 213. To achieve the desired accuracy of ±4 mm depth, it is necessary to measure the width of the catheter tip to at least $\frac{1}{20}^{th}$ of a detector pixel. In order to achieve such sub-pixel accuracy, intensity values in and around cluster image 203 are interpolated by the process of up-sampling in order to increase the number of image pixels. One approach to up-sampling is to linearly interpolate between the original image intensity values at any arbitrary point (x,y) using its four nearest-neighbor pixels. FIG. 23 illustrates and presents the calculations which perform interpolation known as bilinear interpolation. The interpolated intensity value at any point (x,y) is a weighted average of the values of the four nearest-neighbor pixels, with each weighting being proportional to the Cartesian distance from each point. The use of bilinear interpolation in the embodiment C3DLS is not meant to be limiting. Other approaches to interpolation are well known to those skilled in the art of image processing and mathematics and are within the scope of this invention.

In FIG. 23, weightings $Q_{ij}$ are the intensity values of the four nearest-neighbor pixels of point P. Point P is located at (x,y), and $(x_1, y_1)$, $(x_2, y_1)$, $(x_1, y_2)$ and $(x_2, y_2)$ are the coordinates of the nearest-neighbor pixels. When up-sampling is performed with a fineness of 24×24 (i.e., increasing the number pixels by a factor of 24 in each direction), the up-sampled regions of the image contain 24×24 times as many pixels as the originally-captured X-ray image (raw detector pixels). The resulting pixels have a size smaller ($\frac{1}{24}^{th}$) than $\frac{1}{2}^{th}$ of a raw detector pixel, and thus contribute to the sub-pixel accuracy desired.

As an example of determining $N_1$, assume that a cluster is an image of a catheter tip which is physically 8 mm long and that the conical projection geometry of X-ray machine 10 is such that geometric magnification is about 1.4. Thus, the cluster, which is an image of such catheter tip, will be about 1.4×8 mm=11.2 mm long on detector 13. Typical X-ray detectors may have a detector element pitch of 5/mm (detector elements ~0.2 mm×0.2 mm), in which case the cluster will be about 56 pixels long. Assuming that there are about 10 profiles off each end of the cluster and ignoring the angle of the cluster midline for simplicity, if we choose $N_1$ such that each pixel has two intersections, $N_1$ would be about 130. In general, typical catheter tips may be quite a bit smaller than 8 mm so values of $N_1$ may be smaller than this example.

In the embodiment C3DLS 20, in functional block 151 (FIG. 7), up-sampling is shown as being performed along each profile. Up-sampling along each profile 213 saves significant computational time, reduces memory requirements, and contributes to the speed with which the inventive method is performed since large regions of the image do not have to be up-sampled in order to provide the necessary information for each profile 213 which the inventive C3DLS method uses. Such up-sampling along a profile generates 24× the number of pixels along the profile.

Note that functional block 157 of FIG. 7 and functional block 179 of FIG. 8 include up-sampling along different sets of image profiles. The discussion above related to up-sampling also applies to these steps of the inventive method. An alternative embodiment of the inventive method includes the step of up-sampling the entire region around candidate cluster 203 after the expansion of bounding box 207 in functional block 147. This alternative requires significant time and requires more memory to perform the up-sampling but then eliminates the additional along-profile up-sampling of functional blocks 151, 157 and 179.

Referring now to functional block 153 in FIG. 7, sub-pixel statistical edge detection 153 is performed using the up-sampled profiles formed in step 151. Referring again to example profile 213 of FIG. 22, as described above, the $N_1$ profiles 213 are curves representing intensity values along lines perpendicular to longitudinal midline 209. Thus, along each profile 213, in both directions from midline 209, there is an edge point which intersects an edge of cluster 203. In FIG. 22, these two points are referred to as $ep_1$ and $ep_2$. An important part of measuring cluster 203 is identifying the edges of cluster 203. Cluster 203 is an image of a catheter tip (or other medical object being measured) in the plane of detector 13, and the image contains image noise which makes it difficult to determine which pixel represents an edge. However, the important sub-pixel accuracy of edge detection comes about from having a large number of profiles from which edge points are determined and using the large number of points containing sub-pixel information from up-sampling to perform statistical analysis to generate the precise edges of cluster 203.

Another important aspect of sub-pixel statistical edge detection 153 is consistency, from profile-to-profile and image-to-image, in the way in which edge points are determined along profiles 213. In embodiment C3DLS 20 of FIGS. 7 and 8, sub-pixel statistical edge detection 153 is a step which is applied three different times in the analysis of cluster 203, once after each formation of a set of profiles (functional blocks 151, 157 and 179). The steps of this embodiment of sub-pixel statistical edge detection 153 are further detailed in the schematic of FIG. 9 and illustrated using example profile 213 of FIG. 22. The entry and ending points of sub-pixel statistical edge detection 153 are labeled E and F, respectively, in FIG. 9 and as $(E_1, F_1)$, $(E_2, F_2)$ and $(E_3, F_3)$ for functional blocks 153, 157 and 179, respectively, to indicate the three instances of sub-pixel statistical edge detection 153 in C3DLS 20.

Note that for simplicity, example profile 213 as shown in FIG. 22 is drawn as a continuous curve. In reality, profile 213 is an up-sampled pixelated curve, but the continuous representation of FIG. 22 is useful to illustrate the principles of the steps of this embodiment of sub-pixel statistical edge detection 153. Within expanded bounding box 207, the width of profile 213 is such that the ends of profile 213 (to the left and right of FIG. 22) contain enough points to adequately represent the background noise within the image of cluster 203.

Referring now to sub-pixel statistical edge detection 153 in FIG. 9 and to example profile 213 in FIG. 22, in functional block 167, the minimum and maximum pixel intensity values (min and max) for each profile 213 are determined. In functional block 169, a value for the profile intensity range pir=max−min is computed. These three values are illustrated in FIG. 22 for example profile 213. Next, in functional block 171 (FIG. 9), profile widths pw for each profile are determined by selecting points $ep_1$ and $ep_2$ along each profile 213, starting from the center of each profile 213 and moving in each direction along profile 213, i.e., selecting the first points encountered in each direction at which profile 213 is greater than or equal to 55% of the range pir above the minimum min, also indicated in FIG. 22. In FIGS. 9 and 22, 55% is indicated as the fixed percentage of profile intensity range in embodiment C3DLS 20. Other values of the fixed percentage of intensity range may be used, but it has been determined that values around 50-55% are particularly beneficial.

As mentioned above, an example illustrating the general shape of a profile is as shown in FIG. 22. The center of profile 213 is relatively flat with most of the intensity values near 0 corresponding to pixels with almost all X-ray photons blocked by the radio-opaque catheter tip. Profile 213 has generally steep transition regions 214 corresponding to the transition from the radio-opaque catheter tip to the image background. The edges lie within the vertical transition regions 214. The blurring within such transition regions comes about from a number of factors such as detector 13, X-ray source 11 focal spot size, and catheter-tip motion.

For an ideally steep edge, the percentage of profile intensity at which to place edge points is 50%, but many radio-opaque medical objects being imaged do not have such ideally steep edges. For example, catheter tips having circular cross-sections which lessen X-ray absorption at the edges just due to material thickness, and some catheters have outer layers which are not as radio-opaque as metals. Thus, many catheters have transition regions 214 which deviate quite a bit from vertical. This variation in edge transition regions is shown schematically in FIG. 27 in which several idealized profiles 219 with various transition regions 214 are illustrated.

In connection with this invention, as a result of detailed modeling of the X-ray transmission of such objects and with experimentation, it has been found that a pivot point (pivot level) 221 occurs in transition regions 214 at a level other than 50%, but that the pivot behavior of transition regions is robust over a significant range of transition region 214 widths. For example, in modeling a 7 French catheter tip imaged under typical clinical conditions, pivot point 221 was found to occur at a level of about 55%, and this level was robust over a wide range of transition region 214 widths. The existence of pivot point 221 indicates that edge point determination has a degree of insensitivity to medical object edge radio-opacity.

Figure 24:
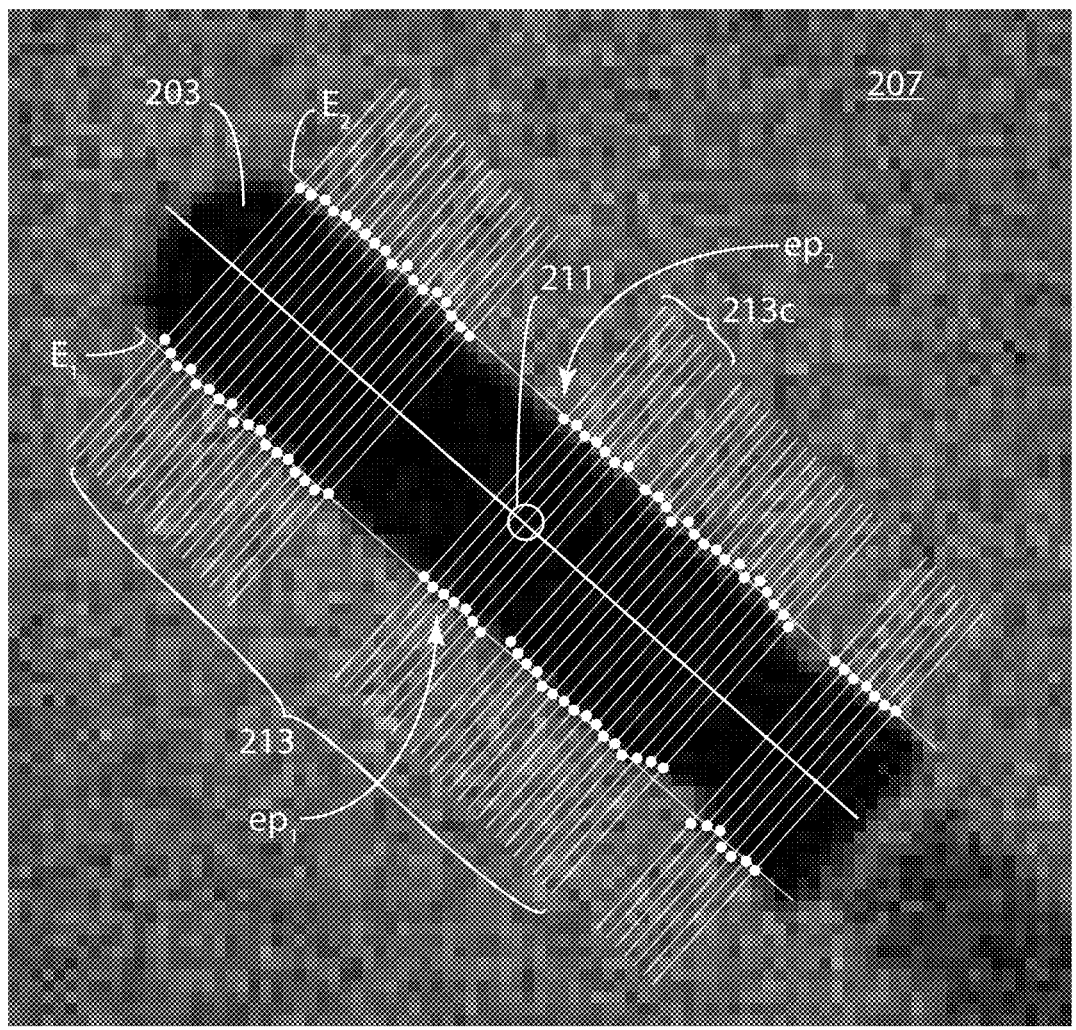
FIG. 24 is an enlargement of the image of FIG. 21, illustrating the steps of sub-pixel statistical edge detection.

FIG. 24 is an enlargement of cluster 203 of FIG. 21 to further illustrate sub-pixel statistical edge detection 153. FIG. 24 includes a larger number of profiles 213 than FIG. 21, but note that FIG. 24 also does not includes all $N_1$ profiles involved in functional blocks 167-177 (FIG. 9) of sub-pixel statistical edge detection 153 in order that the descriptions of the steps can be more easily seen in FIG. 24. (Note that as in FIG. 21, the pixels illustrated are original image pixels, not up-sampled pixels. The same is the case for FIG. 25.)

For each profile 213, a profile width pw is determined as described in functional block 171 of FIG. 9. Edge points $ep_1$ and $ep_2$ on each profile 213 are shown (the arrows point only to one of each such point). In functional block 173, a center width cw is calculated as the average of pw of a percentage of profiles 213 around center 211. In embodiment C3DLS as shown in FIG. 9, 10% of profiles 213 are selected to determine center width cw. These profiles are referred to in FIG. 24 as profiles 213c. The 10% value for this profile 213c selection is not intended to be limiting. Other percentages may be used depending on the nature of the image noise. Center width cw is used to remove profiles the widths pw of which are outliers due to excessive noise in the image of cluster 203. Functional block 175 illustrates the removal of outliers as eliminating from consideration profiles 213 which have pw values outside of the range 0.9 cw to 1.1 cw. Again, the choice of these quantities (0.9 and 1.1) is not intended to be limiting. Other values may be used depending on the noise characteristics of the image.

The final steps (functional blocks 177 and 178) of sub-pixel statistical edge detection 153 use the two sets of edge points $ep_1$ and $ep_2$ of remaining profiles 213 as representations of the two edges $E_1$ and $E_2$ of cluster 203 and compute the least-squares-fit representations of $E_1$ and $E_2$. The analysis involved in performing a least-squares-fit calculation is well known by those skilled in the art of mathematical and graphical analysis.

Referring again to FIG. 7, with points $ep_1$ and $ep_2$ along $E_1$ and $E_2$, the next step is a recomputation of midline 209 using edges $E_1$ and $E_2$ in functional block 155. The new midline 209 is then used to reform and up-sample along a new set of profiles 213 perpendicular to new midline 209 (functional block 157 of FIG. 7) and to repeat sub-pixel statistical edge detection 153 based on these new profiles 213. In parallel to this refinement, the inventive method branches off to steps beginning at point C (see FIG. 8) in order to perform measurements along the longitudinal direction of cluster 203.

In FIG. 8, $N_2$ profiles parallel to new midline 209 are formed and up-sampled in functional block 179. If an edge perpendicular to new midline 209 is to be detected, sub-pixel statistical edge detection 153 is performed as described above on the newly-formed set of profiles parallel to new midline 209. Such profiles are not shown in FIG. 24 since the analysis is identical to that described above for profiles 213. With respect to example cluster 203 in FIG. 24, the transverse edge in the lower right portion of FIG. 24 is detected, and such edge E3 shown in FIG. 25 is calculated as described above.

Figure 25:
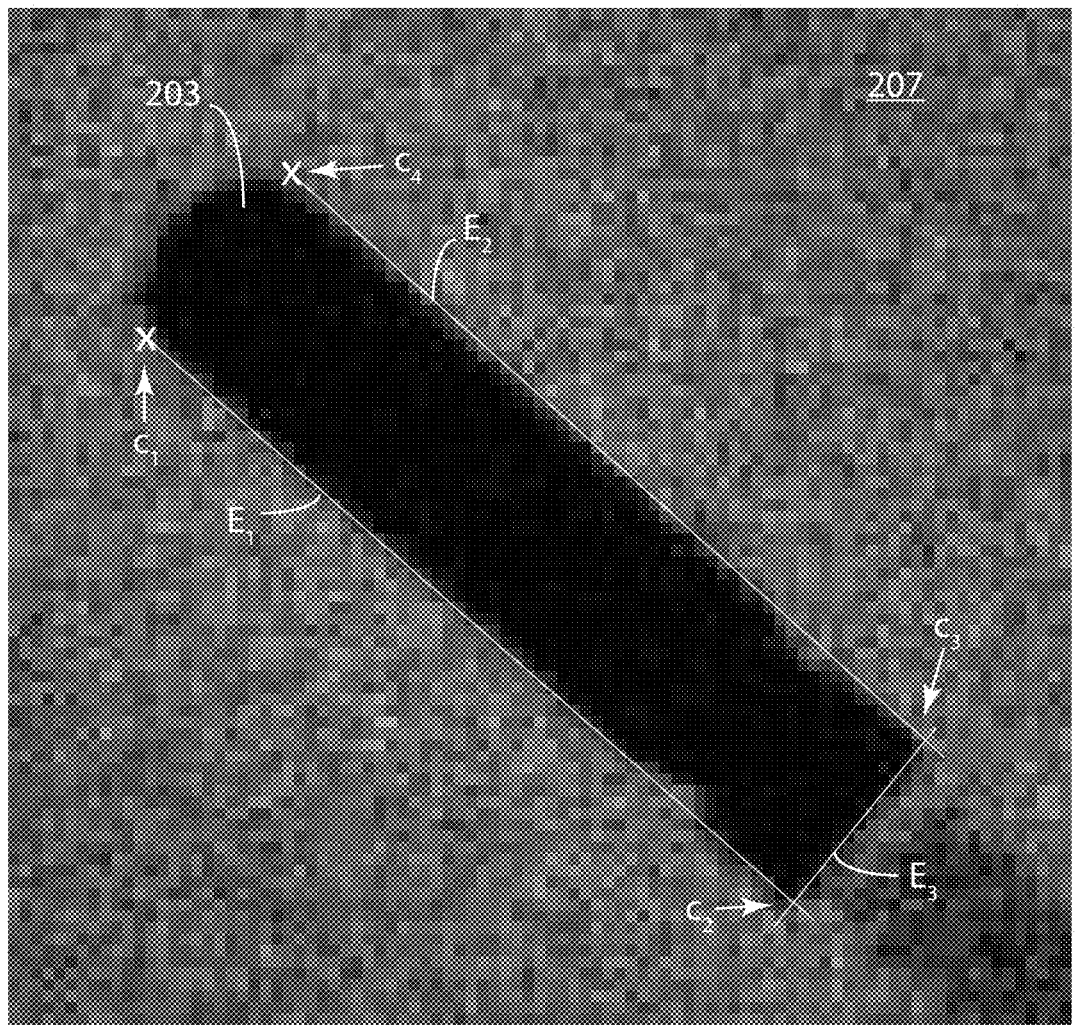
FIG. 25 is the same enlargement as shown in FIG. 24, illustrating the results of sub-pixel statistical edge detection as applied in FIG. 24.

FIG. 25 presents the same original pixel data as is shown in FIG. 24 with simply the final results of all three applications of sub-pixel statistical edge detection 153 overlaid on the image.

Since the catheter tip being tracked in C3DLS has a rounded distal end (as seen in the upper left corner of FIGS. 21, 24 and 25), sub-pixel statistical edge detection 153 treats the distal end of cluster 203 in a modified manner. The rounded edge of the distal end of cluster 203 (corresponding to the distal end of the catheter tip) can be detected in the same manner as described above, and a least-squares fit can be calculated to match an appropriate curve model rather than a straight line. Such modified strategies are within the elements of sub-pixel statistical edge detection 153 as described in FIG. 9. Functional block 178 can be applied with a variety of assumed shape models.

Alternatively, FIG. 25 illustrates an alternative approach to measurement of the distal end. Functional block 183 in FIG. 8 represents the determination of cluster corners based on the calculations of the previous steps. The information from point D as well as information from the steps above functional block 183 in FIG. 8 provide all that is needed for embodiment C3DLS 20 to determine the corners of cluster 203. Corners $c_2$ and $c_3$ are the intersections of $E_3$ with $E_1$ and $E_2$, respectively. $c_1$ and $c_4$ are identified by applying a criterion to the values along $E_1$ and $E_2$ to determine where the curved portion of the distal end begins. This criterion may be, for example, that the corners are the points along $E_1$ and $E_2$ at which the intensity values undergo their final increase from the 0.55 pir+min level. Such criterion is illustrated in FIG. 25. Functional block 183 includes the application of a corner criterion such as this.

Embodiment C3DLS 20 continues in FIG. 8 with functional block 185 which is the computation of cluster length, width, and keystoning based on the coordinates of the corners. Such determinations involve straightforward numerical computations. Keystoning as used herein refers to the variation in width of cluster 203 from end-to-end which indicates out-of-plane angle. The larger (wider) end of cluster 203 is closer to source 11, and the numerical differences are used to compute the out-of-plane angle of the medical object generating cluster 203.

C3DLS 20 continues in functional block 159 with the step of final determination of whether or nor cluster 203 represents a catheter tip by applying the criteria established during initialization steps 41A and 41B (FIG. 5). If cluster 203 is determined to be a catheter tip, C3DLS 20 proceeds to point G in FIG. 4. Also, in functional block 163 of FIG. 8, threshold TH is set to the value found in the first pass of C3DLS 20 up to this point which successfully identifies a catheter tip. If cluster 203 fails to satisfy the criteria in the evaluations of functional block 159, C3DLS 20 proceeds to begin the evaluation of the next cluster to be analyzed, such clusters having been formed in functional block 135 (see FIG. 7).

Figure 26A:
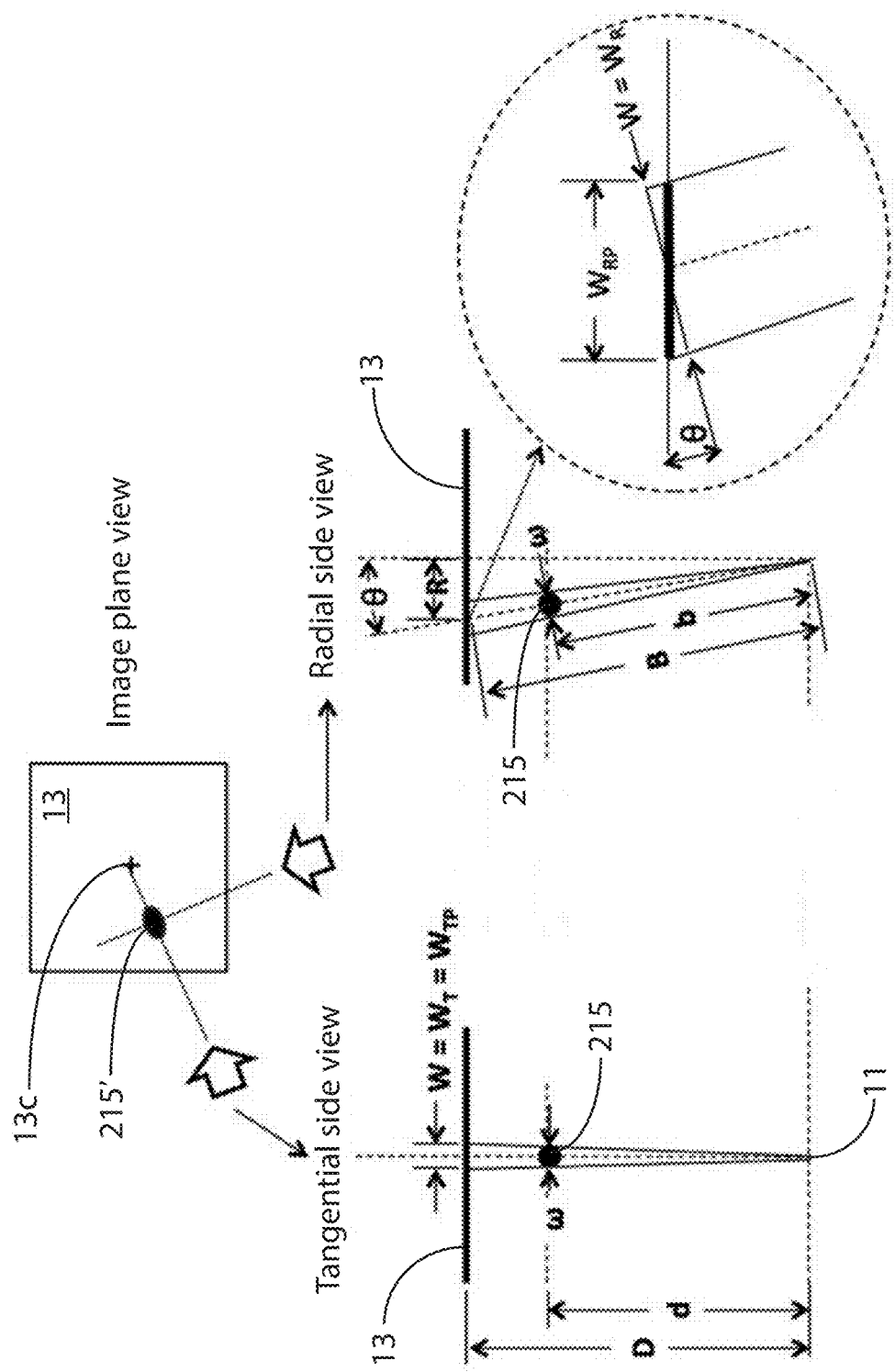
FIG. 26A is a diagram representing the projection geometry of an X-ray machine and illustrating the radial elongation distortion which occurs in such machines. Imaging of a spherical object is illustrated.

Referring again to FIG. 4, C3DLS 20 continues at point G with the measurements determined in functional block 185 of FIG. 8. Using this information on the catheter tip of cluster 203, C3DLS 20 proceeds to apply corrections based on distortion from radial elongation in functional block 31. The process by which the image of a 3D object is projected onto planar detector 13 in conventional X-ray machine 10 is represented in FIG. 26A, illustrating corrections for radial elongation distortion in functional block 31. FIG. 26A includes a sphere 215 as a representative medical object producing an image 215' within the image plane of detector 13. The correction analysis includes consideration of both the radial side view and the tangential side view as indicated in FIG. 26A. An enlargement of a region within the radial side view is shown within the dotted ellipse on the right side of FIG. 26A.

The dimensions of the image of an object projected onto detector 13 depend on the dimensions of the object itself, its rotational orientation relative to detector 13, and the geometric magnification. The rotational orientation of the object can give rise to foreshortening effects. If, for example, a cylindrical object were being imaged, the length of the cylinder in its projected image would depend on the angle between the axis of the cylinder and the plane of detector 13. If the axis were parallel to the plane of detector 13, the length in the image would be given by the actual length of the cylinder times the geometric magnification. However, if the axis of the cylinder were parallel to the X-rays passing through it, the image would be the elliptical or circular cross-section of the cylinder, and all information about its length would be lost.

The only object completely devoid of foreshortening effects is a sphere, since it is rotationally symmetric about any axis through its center. A cylinder is insensitive to foreshortening of its diameter, since a cylinder is rotationally symmetric about its central axis. And, as illustrated in FIG. 26A, the projected 2D image of sphere 215 is an ellipse such as ellipse 215', not a circle. Thus, radial and tangential views differ as shown in FIG. 26A.

Figure 26B:
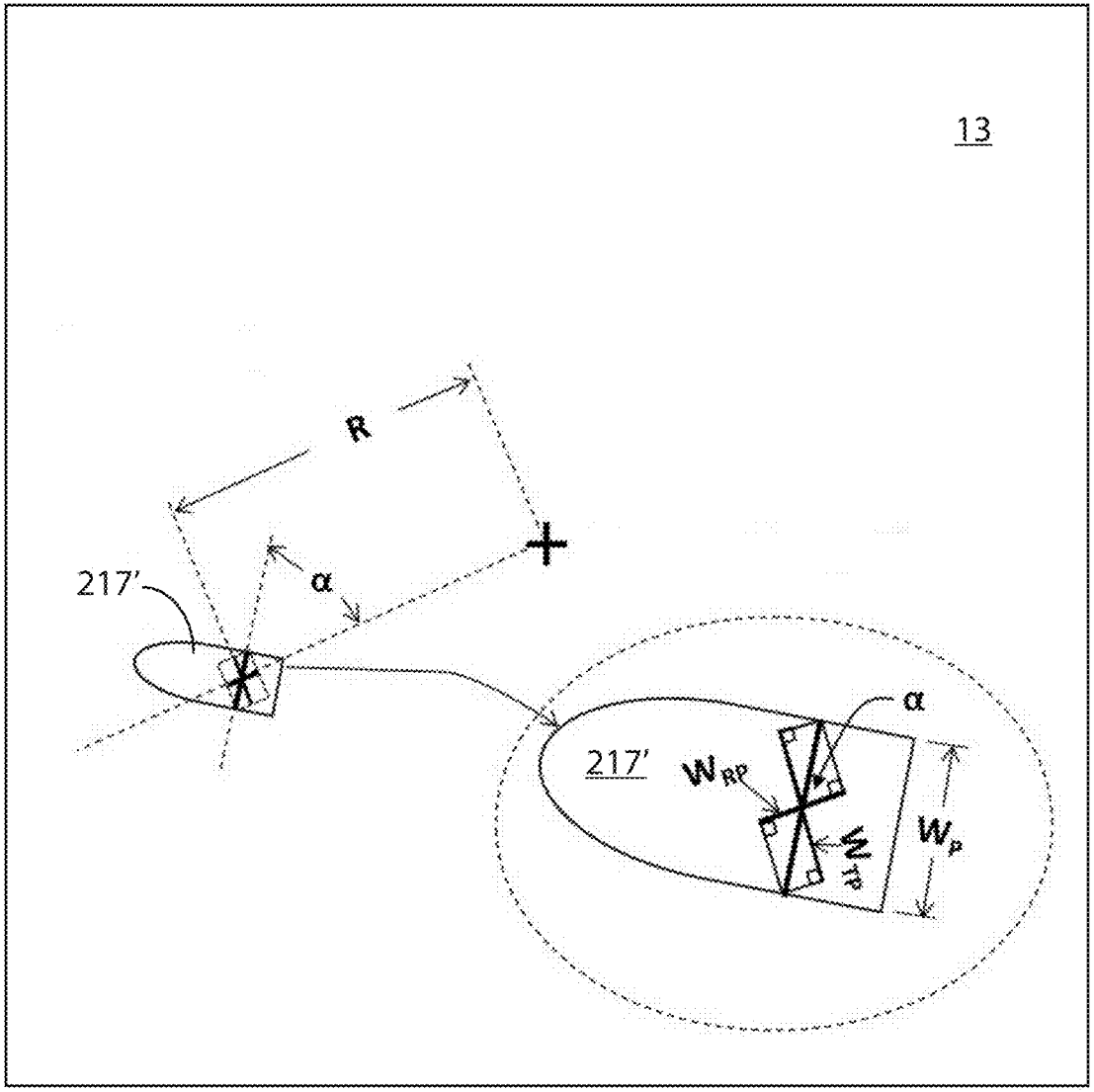
FIG. 26B is a further diagram extending the diagram of FIG. 26A to include the imaging of a cylindrical catheter tip.

FIG. 26B is a diagram illustrating an image 217' of a cylindrical catheter tip in the image plane of detector 13. Image 217' is generated within the geometry of FIG. 26A by replacing sphere 215 with a cylindrical catheter tip (referred to herein as CC) having the same radius as sphere 215.

Figure 27:
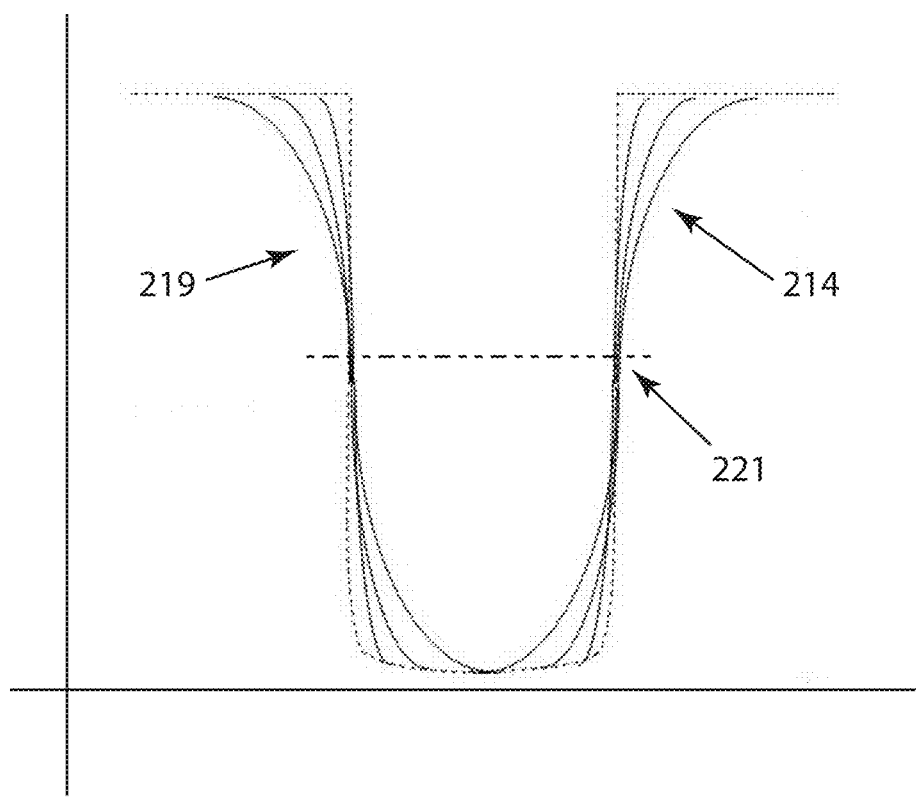
FIG. 27 is a diagram illustrating several idealized cluster profiles and the pivot-point characteristic of edge point determination along intensity profiles.

The following is a list of term definitions for the diagrams of FIGS. 26 and 27:
ω=effective diameter of sphere 215 and CC;
W=diameter of the projection of sphere 215 and CC, measured at the level of detector 13 in a direction perpendicular to a ray passing through the center of sphere 215 or CC—not necessarily in the plane of detector 13;

$W_P$=width of projection 217' measured in the plane of detector 13;

$W_R$=radial component of the width of the projection of CC at the plane of detector 13, perpendicular to the path of the ray passing through its center—not in the plane of detector 13 if R>0;

$W_T$=tangential component of the width of the projection of CC at the plane of detector 13, perpendicular to the path of the ray passing through its center;

$W_{TP}$=width of the projection of sphere 215 and CC measured in the plane of detector 13 in the tangential direction;

$W_{RP}$=width of the projection of sphere 215 and CC measured in the plane of detector 13 in the radial direction;

D=distance from the focal spot of X-ray source 11 to the center 13c of detector 13 where the plane of detector 13 is perpendicular to the central ray running from the focal spot to center 13c of detector 13;

d=distance from the focal spot of X-ray source 11 to the plane passing through sphere 215 or CC where this plane is also parallel to the plane of detector 13;

B=distance from the focal spot of X-ray source 11 to the center of image 215' or 217' at detector 13;

b=distance from the focal spot of X-ray source 11 to the center of sphere 215 or CC;

R=distance between the center of the image 215' or 217' and center 13c of detector 13 in the plane of detector 13;

$\Theta$=angle between the ray passing through the center of sphere 215 or CC and the central ray that intercepts center 13c of detector 13; and $\alpha$=angle between the selected diameter of the image of CC and the radius drawn from center 13c of detector 13 to the center of the selected diameter.

Using these definitions and performing algebraic and trigonometric manipulations well known to those skilled in the art of mathematics yields a relationship for applying radial elongation correction 31 as follows:

$$d = D^*\omega/[W_P \cdot \{[\sin(\alpha)]^2 + [\cos(\alpha)]^2 \cdot [\cos(\Theta)]^2\}^{1/2}]$$

This equation enables calculation of the z-coordinate of a medical object from its image on detector 13, accounting for radial elongation effects and for any orientation of the object within the image on detector 13.

Further, from analysis of the tangential side view in FIG. 26A, the sensitivity of the z-coordinate to changes in $W_{TP}$ is found to be:

$$\delta d/\delta W_{TP} = -d^2/(D \cdot \omega)$$

For typical values for the variables involved, sensitivity $\delta d$ $\delta W_{TP}$ (e.g., mm z per mm diameter) is very large, requiring measurement of effective dimensions on the order of 0.02 mm to achieve the desired operational accuracy of C3DLS 20. Such behavior is due to the fact that the size of a catheter tip is very small compared to the distance between detector 13 and X-ray source 11, which means that the divergence of the beams passing on each side of the catheter tip is small.

In similar fashion, from radial side view analysis, the sensitivity of the z-coordinate to changes in $W_{RP}$ is found to be:

$$\delta d/\delta W_{RP} = -d^2/\{D^*\omega \cdot [1+(R/D)^2]\}$$

Referring again to FIG. 4, functional block 33 is the step of calculating the 3D coordinates and orientation of the medical object being tracked with C3DLS 20. A combination of calculations in functional blocks 31 and 33 produced a set of 3D coordinates for the catheter tip. 3D coordinates are calculated using the four corner points $c_1$, $c_2$, $c_3$ and $c_4$ found in functional block 183 (FIG. 8) and from other measurement quantities found in functional block 185. Sufficient numerical data is available to establish 3D coordinates of the catheter tip.

When 3D coordinates are calculated, such information may be used in a variety of ways such as displaying it as part of other medical display modalities such that it may be used in an interventional procedure such as cardiac ablation. As a medical object such as a catheter is moved inside an anatomical structure such as a chamber of the heart, data may be generated to create 3D maps of such anatomical structures by indicating that a point at which the medical object is positioned is within such structure and marking the 3D coordinates of the catheter tip in memory as a map data point. Map data may then be used by the physician to help in directing the catheter tip to desired points in the anatomical structure. Such images may be integrated with other imaging modalities for enhanced visualization during a variety of medical procedures.

The inventive method processes a selected 2D image as described, making precise measurements of effective medical-object dimensions in order to determine the 3D coordinates and orientation of the medical object. After completion of the processing of a selected image, the inventive system processes a next selected 2D image. Operation may involve processing sequences of images of three to five seconds in length at frames rates of 7.5 to 30 images per second. Such operation enables using multiple images to make measurements of the medical object and performing averaging to reduce variability and increase accuracy.

The method for displaying the mapping and ablation catheter tip in 3D using 2D fluoroscopy alone represent a substantial advantage over other currently available mapping and imaging systems. In particular, the methods provides the physician to use existing equipment in the laboratory without significant infrastructure modification to see the catheter in 3D anatomical structure. While embodiments of the invention are described with reference to the exemplary embodiments using a cardiac catheter, it will be understood by those skilled in the art that small variations may be made to use the inventive method with other radio-opaque medical objects such as leads, stents and other instruments used for interventions and therapy. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims.

The invention claimed is:

1. A method for automatically determining the 3D position and orientation of a radio-opaque medical object in a living body using single-plane fluoroscopy comprising:
   capturing a stream of digitized 2D images from a single-plane fluoroscope;
   detecting an image of the medical object in a subset of the digital 2D images;
   applying to the digital 2D images calculations which preserve original pixel intensity values and permit statistical calculations thereon, the calculations comprising:
     multiple sequential determinations of a midline of the medical object image;
     a plurality of unfiltered raw-data cross-sectional intensity profiles perpendicular to each sequentially-determined midline;

removal of outlier profiles from each plurality of profiles; and statistically combining each plurality of profiles with outliers removed to estimate image dimensions, thereby providing a final estimation of image dimensions to measure the medical-object image;

applying conical projection and radial elongation corrections to the medical-object image measurements; and calculating the 3D position and orientation of the medical object from the corrected 2D image measurements.

2. The method of claim 1 further comprising initialization steps before the detecting step, the initialization steps determining the effective dimensions of the medical-object image and setting medical-object image size-limit criteria.

3. The method of claim 2 wherein, with respect to each 2D image in the subset, the detecting step includes:

applying a threshold filter to the 2D image;

forming clusters of image pixels;

evaluating each of the clusters against the medical-object image size-limit criteria; and selecting the cluster that contains the image of the medical object.

4. The method of claim 3 further including computing center, longitudinal midline and bounding-box data of the selected cluster.

5. The method of claim 4 wherein the measuring step further includes applying the center, midline and bounding-box data to the unfiltered 2D image, expanding the bounding box area around the medical-object image, and up-sampling such 2D image.

6. The method of claim 5 wherein the up-sampling is performed only along each cross-sectional image profile perpendicular to the midline.

7. The method of claim 5 further including identifying medical-object image edges by selecting edge points on each profile at a fixed percentage of profile intensity range.

8. The method of claim 7 wherein the profile intensity range of a profile is the difference between the maximum and minimum intensity values for such profile.

9. The method of claim 8 wherein identifying medical-object image edges substantially parallel to the midline includes computing least-squares-fit representations of the edges.

10. The method of claim 9 wherein the measuring step further includes the steps of (a) recomputing the medical-object image center based on the least-squares-fit edges and (b) determining medical-object image width, length and keystoning in the 2D image.

11. The method of claim 9 wherein the up-sampling is performed only along each cross-sectional image profile perpendicular to the midline.

12. The method of claim 5 further including:

forming a plurality of cross-sectional image profiles parallel to the midline;

identifying medical-object edges substantially perpendicular to the midline; and computing least-squares-fit representations of the edges substantially perpendicular to the midline.

13. The method of claim 12 wherein the measuring step further includes recomputing the medical-object image center based on the least-squares-fit edges and determining medical-object image width, length and keystoning in the 2D image.

14. The method of claim 12 wherein up-sampling is performed only along each cross-sectional image profile perpendicular to the midline.

15. The method of claim 1 wherein the subset of 2D images is selected by respiration gating from a respiration signal from the living body.

16. The method of claim 1 wherein the subset of 2D images is selected by cardiac gating from an ECG signal from the living body.

17. The method of claim 16 wherein the subset of 2D images is selected by R-wave gating.

18. The method of claim 17 wherein the R-wave gating is by an R-wave gating process having a threshold to which the ECG signal is compared and the threshold is independent of levels of the ECG signal at which previous R-wave triggers occurred.

19. The method of claim 1 further including creating a 3D map of an anatomical structure within the living body.

20. The method of claim 19 further including the step of displaying the 3D map on a display device.

21. The method of claim 19 further including the step of displaying the 3D position and orientation on the display device.

22. The method of claim 19 wherein the anatomical structure is a cardiac structure.

23. The method of claim 22 further including the step of displaying the 3D map on a display device.

24. The method of claim 1 wherein the step of applying measurement corrections includes correcting medical-object image measurements for out-of-plane angle.

25. The method of claim 1 further including the steps of capturing, detecting, applying geometric calculations, applying corrections, and calculating 3D position and orientation multiple times with the medical object in a single position and averaging the calculated 3D position and orientation data, thereby to enhance accuracy of the determination.

* * * * *